United States Patent [19]
Kun

[11] Patent Number: 5,908,861
[45] Date of Patent: Jun. 1, 1999

[54] METHODS FOR TREATING INFLAMMATION AND INFLAMMATORY DISEASE USING PADPRT INHIBITORS

[75] Inventor: Ernestt Kun, Mill Valley, Calif.

[73] Assignee: Octamer, Inc., Berkeley, Calif.

[21] Appl. No.: 08/855,616

[22] Filed: May 13, 1997

[51] Int. Cl.⁶ .......................... A61K 31/47; A61K 31/35; A61K 31/165

[52] U.S. Cl. .......................... 514/456; 514/309; 514/617; 514/619; 514/622; 514/825; 514/898

[58] Field of Search ..................... 514/456, 825, 514/898, 309, 617, 619, 622

[56] References Cited

U.S. PATENT DOCUMENTS

| | | | |
|---|---|---|---|
| 5,262,564 | 11/1993 | Kun et al. | 562/430 |
| 5,464,871 | 11/1995 | Kun et al. | 514/617 |
| 5,473,074 | 12/1995 | Kun et al. | 546/141 |
| 5,482,975 | 1/1996 | Kun et al. | 514/619 |
| 5,484,951 | 1/1996 | Kun et al. | 549/285 |
| 5,516,941 | 5/1996 | Kun et al. | 564/166 |
| 5,583,155 | 12/1996 | Kun et al. | 514/457 |

OTHER PUBLICATIONS

CA 116:262534, Clemens et al., Mar. 1992.
CA 113:40476, Friary, Jan. 1990.
Anderson, et al., "Selective Inhibition of Cyclooxygenase (COX)–2 Reverses Inflammation and Expression of COX–2 and Interleukin 6 in Rat Adjuvant Arthritis." *J. Clin. Invest.*—97(11):2672–2679 (1996).
Baeuerle, et al., "Function and Activation of NF-$_k$B in the Immune System," *Ann. Rev. Immunol.*—12:141–179 (1994).
Bauer, et al., "Modification of Growth Related Enzymatic Pathways and Apparent Loss of Tumorigenicity of a ras–Transformed Bovine Endothelial Cell Line by Treatement with 5–Iodo–6–Amino–1,2–Benzopyrone (INH$_2$BP)," *Int. J. Oncol.*—8:239–252 (1996).
Berger, "Oxidant–Induced Cytotoxicity: A Challenge for Metabolic Modulation," *Am. J. Respir. Cell Mol. Biol.*—4:1–3 (1991).
Beutler, "TNF, Immunity and Inflammatory Disease: Lessons of the Past Decade," *J. Investigative Medicine*—43(3): 227–235 (1995).
Brahn, et al., Animal Models of Rheumatoid Arthritis, *Clin. Orthop. Rel. Res.*—265:52–53 (1991).
Buki, et al., "Identification of Domains of Poly(ADP–Ribose) Polymerase for Protein Binding and Self–Association," *J. Biol. Chem.*—270(7):337–3377 (1995).
Cochrane, et al., "Mechanisms of Oxidant Injury of Cells," *Molec. Aspects Med.*—12:137–147 (1991).
Conner, et al., "Suppression of Adjuvant–Induced Arthritis by Selective Inhibition of Inducible Nitric Oxide Synthase," *Eur. J. Pharmacol.*—273:15–24 (1995).
Cowley, et al., "Activation of MAP Kinase Kinase is Necessary and Sufficient for PC12 Differentiation and for Transformation of NIH 3T3 Cells," *Cell*—77:841–852 (1994).
Crow, et al., "The Role of Peroxynitrite in Nitric Oxide–Mediated Toxicity," *Current Top Microbiol. Immunol.*—196:57–73 (1995).
Farrell, et al., "Increased Concentration of Nitrite in Synovial Fluid and Serum Samples Suggest Increased Nitric Oxide Synthesis in Rheumatic Diseases," *Ann. Rhem Dis.*—51:1219–1222 (1992).
Ferrell, "Tripping the Switch Fantastic: How a Protein Kinase Cascade Convert Graded Inputs Into Switch–Like Outputs," *TIBS*—21:460–466 (1996).
Giroir, et al., "Mediators of Septic Shock: New Approaches for Interrupting the Endogenous Inflammatory Cascade," *Critical Car. Med.*—21(5):780–789 (1993).
Grabowski, et al., "Nitric Oxide Production in Cells Derived from the Human Joint," *Br. J. Rheumatol.*—35:207–212 (1996).
Griffin, et al., "The in vitro Effect of Benzamide and Phenobarbital on Liver Enzymes: Poly(ADP–Ribose) Polymerase, Cytochrome P–450, Styrene Oxide Hydrolase, Glutathione S–transferase and UDP–Glucuronyl Transferase," *Biochem. Biophys. Res. Comm.*—122(2):770–775 (1984).
Hauschildt, et al., "Induction of Nitric oxide Synthase in L929 Cells by Tumour–Necrosis Factor α is Prevented by Inhibitors of Poly(ADP–Ribose) Polymerase," *Biochem. J.*—288:255–260 (1992).
Häuselmann, et al., "Nitric Oxide and Proteoglycan Biosynthesis by Human Articular Chondrocytes in Alginate Culture," *FEBS Lett.*—352:361–364 (1994).
Kaur, et al., "Evidence for Nitric Oxide–Medicated oxidative Damage in Chronic Inflammation—Nitrotyrosine in Serum and Synovial Fluid from Rheumatoid Patients," *FEBS Lett.*—350:9–12 (1994).
Kawai, et al., "Enhancement of Rat Urinary Bladder Tumorigenesis by Lipopolysaccharide–Induced Inflammation," *Cancer Res.*—53:5172–5175 (1993).
Kyriakis, et al., "Sounding the Alarm: Protein Kinase Cascades Activated by Stress and Inflammation," *J. Biol. Chem.*—271(40):24313–24316 (1996).
L'Allemain, "Deciphering the Map Kinase Pathway," *Prog. Growth Factor Res.*—5:291–334 (1994).
Levitzki, et al., "Signal–Transduction Therapy—A Novel Approach to Disease Management," *Eur. J. Biochem.*—226:1–13 (1994).
Liles, et al., "Review: Nomenclature and Biologic Significance of Cytokines Involved in Inflammation and the Host Immune Response," *J. Infect Dis.*—172:1573–1580 (1995).

(List continued on next page.)

*Primary Examiner*—Kimberly Jordan
*Attorney, Agent, or Firm*—Albert P. Halluin; Howrey & Simon

[57] ABSTRACT

The present invention is directed to a method for treating inflammation or inflammatory disease in an animal or mammal, which comprises the steps of administering an effective amount of an pADPRT inhibitory compound to said animal or mammal.

11 Claims, 9 Drawing Sheets

OTHER PUBLICATIONS

Lindahl, et al., "Post–Translational Modification of Poly-(ADP–Ribose) Polymerase Induced by DNA Strand Breaks," *Trends Biochem. Sci.*—20:405–411 (1995).

Liu, et al., "Woodchuck Hepatitis Virus Surface Antigen Induces Nitric Oxide Synthesis in Hepatocytes: Possible Role in Hepatocarcinogenesis," *Carcinogenesis*—15(12):2875–2877 (1994).

Lowenstein, et al., "Macrophase Nitric Oxide Synthase Gene: Two Upstream Regions Mediate Induction by Interferon γ and Lipopolysaccharide," *Proc. Natl. Acad. Sci.*—90:9730–9734 (1993).

Marczin, et al., "Tyrosine Kinase Inhibitors Suppress Endotoxin—and IL–1β–Induced NO Synthesis in Aortic Smooth Muscle Cells," *Am. J. Physiol.*—265:H1014–1018 (1993).

Martin, et al., "Role of Interferon Regulatory Factor 1 in Induction of Nitric Oxide Synthase," *J. Exp. Med.*—180:977–984 (1994).

Matsuda, et al., "Signaling Pathways Mediated by the Mitogen–Activated Protein (MAP) Kinase Kinase/MAP Kinase Cascade," *J. Leukocyte Biology*—56:548–553 (1994).

McCartney–Francis, et al., "Suppression of Arthritis by an Inhibitor of Nitric Oxide Synthase," *J. Exp. Med.*—178:749–754 (1993).

Miesel, et al., "Effects of Allopurinol on in vivo Suppression of Arthritis in Mice and ex vivo Modulation of Phagocytic Production of Oxygen Radicals in Whole Human Blood," *Inflammation*—18(6):597–612 (1994).

Muller, et al., "Nuclear Factor Kappa β, a Mediator of Lipopolysaccharide Effects," *Immunobiol.*—187:233–256 (1993).

Murrell, et al., "Nitric Oxide: An Important Articular Free Radical," *J. bone Joint Sur.–Am.*—78:265–274 (1996).

Nathan, "Nitric Oxide as a Secretory Product of Mammalian Cells," *FASEB J.*—6:3051–3064 (1992).

Novogrodsky, et al., "Prevention of Lipopolysaccharide–Induced Lethal Toxicity by Tyrosine Kinase Inhibitors," *Science*—264:1319–1322 (1994).

Ohshima, et al., "Chronic Infections and Inflammatory Processes as Cancer Risk Factors: Possible Role of Nitric Oxide in Carcinogenesis," *Mutation Res.*—305:253–264 (1994).

Oyanagui, "Nitric Oxide and Superoxide Radical are Involved in Both Initiation and Development of Adjuvant Arthritis in Rats," *Life Sci.*—54(17):PL285–L289 (1994).

Pang, et al., "Inhibition of MAP Kinase Kinase Blocks the Differentiation of PC–12 Cells Induced by Nerve Growth Factor," *J. Biol. Chem.*—270(23):13585–13588 (1995).

Pellat–Deceunynck, et al., "Nicotinamide Inhibits Nitric Oxide Synthase mRNA Induction in Activated Macrophages," *Biochem. J.*—297:53–58 (1994).

Pryor, et al., "The Chemistry of Peroxynitrite: A Product from the Reaction of Nitric Oxide with Superoxide," *Am. J. Physiol.*—L699–L772 (1995).

Rosin, et al., "Inflammation, Chromosomal Instability, and Cancer: The Schistosomiasis Model," *Cancer Res.*—54:1929s–1933s (1994).

Saklatvala, et al., "Interleukin 1 and Tumour Necrosis Factor Activate the Mitogen–Activated Protein (MAP) Kinase Kinase in Cultured Cells," *FEBS*—334(2):189–192 (1993).

Sakurai, et al., "Nitric Oxide Production and Inducible Nitric Oxide Synthase Expression in Inflammatory Arthritides," *J. Clin. Invest.*—96:2357–2363 (1995).

Singh, et al., "Regulation of Cytokine–Inducible Nitric Oxide Synthase in Cardiac Myocytes and Microvascular Endothelial Cells," *J. Biol. Chem.*—271(2):1111–1117 (1996).

Southan, et al., "Spontaneous Rearrangement of Aminoalkylisothioureas into Mercaptoalkylguanidines, a Novel Class of Nitric Oxide Synthase Inhibitors with Selectivity Towards the Inducible Isoform," *Br. J. Pharmacol.*—(1996).

Stefanovic–Racic, et al., "Nitric Oxide and Arthritis," *Arthr. Rhemat.*—36(8):1036–1044 (1993).

Stefanovic–Racic, et al., "N–Monomethyl Arginine, an Inhibitor of Nitric oxide Synthase, Suppresses the Development of Adjuvant Arthritis in Rats," *Arthr. Rhemat.*—37:1062–1069 (1994).

Stichtenoth, et al., "Urinary Nitrate Excretion is Increased in Patients with Rheumatoid Arthritis and Reduced by Prednisolone," *Ann Rhem. Dis.*—54:820–824 (1995).

Szabo, et al., "Isoproterenol Regulates Tumour Necrosis Factor, Interleukin–10, Interleukin–6 and Nitric Oxide Production and Protects Against the Development of Vascular Hyporeactivity in Endotoxaemia," *Immunology*—90:950–100 (1997).

Szabo, et al., "DNA Strand Breakage, Activation of Poly-(ADP–Ribose) Synthetase, and Cellular Energy Depletion are Involved in the Cytotoxicity in Macrophases and Smooth Muscle Cells Exposed to Peroxynitrite," *Proc. Natl. Acad.*—93:1753–1758 (1996).

Szabo, et al., "Inhibition by Spermine of the Induction of Nitric Oxide Synthase in J774.2 Macrophages: Requirement of a Serum Factor," *Br. J. Pharmacol.*—112:355–356 (1994).

Ueda, et al., "ADP–Ribosylation," *Ann. Rev. Biochem.*—54:73–100 (1985).

Vane, et al., "New Insights into the Mode of Action of Anti–Inflammatory Drugs," *Inflamm. Res.*—44:1–10 (1995).

Weinberg, et al., "The Role of Nitric Oxide in the Pathogenesis of Spontaneous Murine Autoimmune Disease: Increased Nitric Oxide Production and Nitric Oxide Synthase Expression in MRL–lpr/1pr Mice, and Reduction of Spontaneous Glomerulonephritis and Arthritis by Orally Administered $N^G$–Monomethyl–L–Arginine," *J. Exp. Med.*—179:651–660 (1994).

Whiteman, et al., "Protection Against Peroxynitrite Dependent Tyrosine Nitration and $α_1$–Antiporteinase Inactivation by Some Anti–Inflammatory Drugs and by the Antibiotic Tetracycline," *Ann. Rhem. Dis.*—55:383–387 (1996).

Willis, et al., "Differential Induction of the Mitogen–Activated Protein Kinase Pathway by Bacterial Lipopolysaccharide in Culture Monocytes and Astrocytes," *Biochem. J.*—313:519–524 (1996).

Zingarelli, et al., "Peroxynitrite–Mediated DNA Strand Breakage Activates Poly–Adenosine Diphosphate Ribosyl Synthetase and Causes Cellular Energy Depletion in Macrophages Stimulated with Bacterial Lipopolysaccharide," *J. Immunol.*—156:350–358 (1996).

METHODS FOR TREATING INFLAMMATION AND INFLAMMATORY DISEASE USING PADPRT INHIBITORS

The present invention relates to methods for treating inflamation and inflammatory diseases, including arthritis, in animals or mammals. The invention also relates to methods for treating animals or mammals having both gram negative and gram positive endotoxin symptoms resulting from systemic infections or resulting from infestation by lipopolysaccharides. These methods involve the use of therapeutically effective amounts of pADPRT inhibitory compounds.

BACKGROUND OF THE INVENTION

The use of pADPRT inhibitory compounds have been reported for treating cancer and viral infections. Examples of these methods are described in U.S. Pat. Nos. 5,464,871; 5,473,074; 5,482,975; 5,484,951; 5,516,941; and 5,583,155, the disclosures of which are incorporated herein by reference.

In the published literature, 5-iodo-6-amino-1,2-benzopyrone (INH$_2$BP), a novel inhibitor of the nuclear enzyme poly-ADP ribose polymerase (pADPRT) has recently been shown to inhibit in vivo tumorigencity in a Ha-ras transfected endothelial cell line; Bauer et al., 1995, "Modification of growth related enzymatic pathways and apparent loss of tumorigenicity of a ras-transformed bovine endothelial cell line by treatment with 5-iodo-6-amino-1,2-benzopyrone (INH$_2$BP)," *Int. J. Oncol.* 8:239–252; Bauer et al., 1995, "Reversal of malignant phenotype by 5-iodo-6-amino-1,2-benzopyrone, a non-covalently binding ligand of poly (ADP-ribose) polymerase," *Biochimie* 77:347–377. Treatment with INH$_2$BP has also resulted in changes in topoisomerase I and II and MAP kinase activity; Bauer et al., 1995, "Modification of growth related enzymatic pathways and apparent loss of tumorigenicity of a ras-transformed bovine endothelial cell line by treatment with 5-iodo-6-amino-1,2-benzopyrone (INH$_2$BP)," *Int. J. Oncol.* 8:239–252; Bauer et al., 1995, "Reversal of malignant phenotype by 5-iodo-6-amino-1,2-benzopyrone, a non-covalently binding ligand of poly (ADP-ribose) polymerase," *Biochimie* 77:347–377. Based on the effects observed, a hypothesis regarding the potential use of INH$_2$BP in the therapy of cancer has been put forward; Bauer et al., 1995, "Modification of growth related enzymatic pathways and apparent loss of tumorigenicity of a ras-transformed bovine endothelial cell line by treatment with 5-iodo-6-amino-1,2-benzopyrone (INH$_2$BP)," *Int. J. Oncol.* 8:239–252; Bauer et al., 1995, "Reversal of malignant phenotype by 5-iodo-6-amino-1,2-benzopyrone, a non-covalently binding ligand of poly (ADP-ribose) polymerase," *Biochimie* 77:347–377.

Malignant growth and inflammatory processes share the activation of certain cellular signal transduction pathways, e.g., MAP kinase; Kyriakis et al., 1996, "Sounding the alarm: protein kinase cascades activated by stress and inflammation," *J. Biol Chem.* 271:24313–24316; Ferrell, J E, 1996, "Tripping the switch fantastic: how a protein kinase cascade can convert graded inputs into switch-like outputs," *TIBS* 21:460–466. Chronic inflammation frequently leads to carcinogenic transformation, as demonstrated, for example, in the case of the intestinal epithelium; Kawai et al., 1993, "Enhancement of rat urinary bladder tumorigenesis by lipopolysaccharide-induced inflammation," *Cancer Res.* 53:5172–5; Rosin et al., 1994, "Inflammation, chromosomal instability, and cancer: the schistosomiasis model," *Cancer Res.* 54 (7 Suppl):1929s–1933s; Choi et al., 1994, "Similarity of colorectal cancer in Crohn's disease and ulcerative colitis: implications for carcinogenesis and prevention," *Gut* 35:950–4. Based on the connection between chronic inflammation and carcinogenic transformation, the aim of the present study was to investigate whether INH$_2$BP affects the course of the inflammatory process in vitro and in vivo. In our study, the production of multiple proinflammatory mediators was induced by bacterial lipopolysaccharide (endotoxin, LPS). LPS is known to induce a multitude of cellular reactions and triggers a systemic inflammatory response. LPS-induced pro-inflammatory mediators include tumor necrosis factor alpha (TNF), interleukin-1, interferon-gamma, whereas antiinflammatory mediators include interleukin-10 (IL-10) and interleukin-13; Deltenre et al., 1995, "Gastric carcinoma: the Helicobacter pylori trail," *Acta Gastroenterol Belg.* 58:193–200; Beutler, 1995, "TNF, immunity and inflammatory disease: lessons of the past decade," *J. Invest. Med.* 42:227–35; Liles et al., 1995, "Review: nomenclature and biologic significance of cytokines involved in inflammation and the host immune response," *J. Infect Dis.* 172:1573–80; Giroir, 1993, "Mediators of septic shock: new approaches for interrupting the endogenous inflammatory cascade," *Critical Car. Med.* 21:780–9. As a consequence of the production of these inflammatory cytokines, LPS initiates the production of inflammatory free radicals (oxygen-centered, such as superoxide, and nitrogen-centered radicals, such as nitric oxide [NO]) and of prostaglandins; Nathan, 1992, "Nitric oxide as a secretory product of mammalian cells," *FASEB J.* 6:3051–3064; Vane, J. R., The Croonian Lecture 1993, "The endothelium: maestro of the blood circulation," *Proc. Roy. Soc. Lond B* 343:225–246; Szabo, C.; 1995, "Alterations in the production of nitric oxide in various forms of circulatory shock," *New Horizons* 3:3–32. The production of NO in inflammation is due to the expression of a distinct isoform of NO synthase (iNOS), while the production of inflammatory cytokines is explained by the expression of a distinct isoform of cyclooxygenase (cyclooxygenase-2, COX-2); Nathan, 1992, "Nitric oxide as a secretory product of mammalian cells," *FASEB J.* 6:3051–3064; Vane, J. R., The Croonian Lecture 1993, "The endothelium: maestro of the blood circulation," *Proc. Roy. Soc. Lond B* 343:225–246; Szabo, C.; 1995, "Alterations in the production of nitric oxide in various forms of circulatory shock," *New Horizons* 3:3–32. iNOS, COX-2, as well as the above mentioned pro-inflammatory cytokines and free radicals which play an important role in the LPS-induced inflammatory response; ; Nathan, 1992, "Nitric oxide as a secretory product of mammalian cells," *FASEB J.* 6:3051–3064; Vane, J. R., The Croonian Lecture 1993, "The endothelium: maestro of the blood circulation," *Proc. Roy. Soc. Lond B* 343:225–246; Szabo, C.; 1995, "Alterations in the production of nitric oxide in various forms of circulatory shock," *New Horizons* 3:3–32. Moreover, NO (or its toxic byproduct, peroxynitrite), has been implicated as a key mediator leading to the transformation of the inflammatory response into a carcinogenic process; Bartsch et al., 1994, "Endogenously formed N-nitroso compounds and nitrosating agents in human cancer etiology," *Pharmacogenetics* 2:272–7; Liu et al., 1992, "Woodchuck hepatitis virus surface antigen induces NO synthesis in hepatocytes: possible role in hepatocarcinogenesis.," *Carcinogenesis* 15:2875–7; Ohshima et al., 1994, "Chronic infections and inflammatory processes as cancer risk factors: possible role of nitric oxide in carcinogenesis," *Mutation Res.* 305:253–64. In the current studies, we have first investigated whether treatment with INH₂BP affects the production of the inflammatory mediators tumor necrosis factor alpha [TNF], interleukin-10, interleukin-6, NO, and prostaglandin in vivo, in LPS-induced models of inflammation.

There are a multitude of intracellular processes which precede the production of proinflammatory mediators. Activation of tyrosine kinases; Levitzki, A., 1994, "Signal-transduction therapy. A novel approach to disease management," *Eur. J. Biochem.* 226:1–13; Novogrodsky et al., 1994, "Prevention of lipopolysaccharide-induced lethal toxicity by tyrosine kinase inhibitors," *Science* 264 (Wash) :1319–22; Marczin et al., 1993, "Tyrosine kinase inhibitors suppress endotoxin- and IL-1beta-induced NO synthesis in aortic smooth muscle cells," *Am. J. Physiol.* 265:H1014–1018; mitogen-activated protein kinase (MAP kinase); Matsuda et al., 1994, "Signaling pathways mediated by the mitogen-activated protein (MAP) kinase kinase/MAP kinase cascade," *J. Leukocyte Biol.* 56:548–53; L'Allemain, G., 1994, "Deciphering the MAP kinase pathway," *Progr. Growth Factor Res.* 5:291–334; Cowley et al., 1994, "Activation of MAP kinase kinase is necessary and sufficient for PC12 differentiation and for transformation of NIH 3T3 cells.," *Cells* 77:841–52; and the nuclear factor kappa B (NF-kB) pathway; Baeuerle et al., 1994, "Function and activation of NF- B in the immune system," *Ann. Rev. Immunol.* 12:141–79; Schreck et al., 1992, "Nuclear factor kappa B: an oxidative stress-responsive transcription factor of eukaryotic cells (a review)," *Free Radical Res. Comm.* 17:221–37; Muller et al., 1993, "Nuclear factor kappa B, a mediator of lipopolysaccharide effects," *Immunobiol.* 187:233–56; are recognized as important factors in the inflammatory response and contribute to the expression or production of inflammatory mediators. Therefore, we have also investigated whether INH₂BP also affects the LPS-induced activation of MAP kinase and the NF-kB by LPS. The results of the current study demonstrate that INH₂BP has potent antiinflammatory effects by modulating multiple components of the LPS-induced inflammatory response.

SUMMARY OF THE INVENTION

One aspect of the invention is a method for treating inflamation or inflammatory disease in an animal or mammal, which comprises the steps of administering an effective amount of an pADPRT inhibitory compound to said animal or mammal.

Another aspect of the invention is a method for treating inflamation or inflammatory disease in an animal or mammal, which comprises the steps of administering an effective amount of a pADPRT inhibitory compound wherein the pADPRT inhibitory compound is selected from the group consisting of:

a compound having the formula:

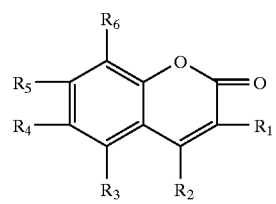

wherein $R_1$, $R_2$, $R_3$, $R_4$, $R_5$ and $R_6$ are each selected from the group consisting of hydrogen, hydroxy, amino, alkyl, alkoxy, cycloalkyl or phenol, optionally substituted with alkyl, alkoxy, hydroxy or halo, and only one of $R_1$, $R_2$, $R_3$, $R_4$, $R_5$ and $R_6$ is amino; a compound having the formula:

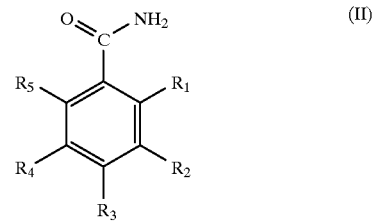

wherein $R_1$, $R_2$, $R_3$, $R_4$, and $R_5$ are each selected from the group consisting of hydrogen, hydroxy, amino, alkyl, alkoxy, cycloalkyl or phenol, optionally substituted with alkyl, alkoxy, hydroxy or halo, and only one of $R_1$, $R_2$, $R_3$, $R_4$, and $R_5$ is amino; and a compound having the formula:

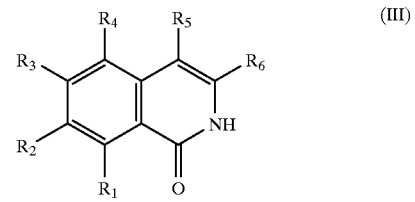

wherein $R_1$, $R_2$, $R_3$, $R_4$, and $R_5$ and $R_6$ are each selected from the group consisting of hydrogen, hydroxy, amino, alkyl, alkoxy, cycloalkyl or phenol, optionally substituted with alkyl, alkoxy, hydroxy or halo, and only one of $R_1$, $R_2$, $R_3$, $R_4$, and $R_5$ is amino.

Preferred pADPRT compounds include: 6-amino-1,2-benzopyrone, 3-nitrosobenzamide, 5-amino-1(2H)-isoquinolinone, 7-amino-1(2H)-isoquinolinone, and 8-amino-1(2H)-isoquinolinone.

Still another aspect of the invention includes a method of treating both gram negative and gram positive induced symptoms in an animal or mammal, said method comprising the step of administering to an animal or mammal a therapeutically effective amount of a pADPRT inhibitory compound.

Still another aspect of the invention is a method of treating both gram negative and gram positive induced endotoxin symptoms in an animal or mammal which comprises the step of administering to an animal or mammal a therapeutically effective amount of a pADPRT inhibitory compound wherein the compound is selected from the group consisting of compound I, compound II, or compound III, as described above.

Still another aspect of the invention is a method of treating both gram negative and gram positive induced endotoxin symptoms in an animal or mammal which comprises the step of administering to an animal or mammal a therapeutically effective amount of a pADPRT inhibitory compound wherein the compound has the structural formula noted above as compounds I, II or III.

Still another aspect of the invention is a method of treating arthritis in an animal or mammal comprising the step of administering an effective amount of or an pADPRT inhibitory compound wherein the compound has the structural formula noted above as compounds I, II or III.

Still another aspect of the invention is a method of treating Chron's Disease in an animal or mammal comprising the step of administering an effective amount of an pADPRT inhibitory compound wherein the compound has the structural formula noted above as compounds I, II or III.

Still another aspect of the invention is a method of treating Barrett's Disease in an animal or mammal comprising the step of administering an effective amount of an pADPRT inhibitory compound wherein the compound has the structural formula noted above as compounds I, II or III.

The pADPRT inhibitory compounds of the invention may be prepared by the methods described in U.S. Pat. Nos. 5,464,871; 5,473,074; 5,482,975; 5,484,951; 5,516,941; and 5,583,155, the disclosures of which are incorporated herein by reference.

The preferred compounds for use in the methods of the invention include those where the halo group is iodo, and one of the R groups is amino, one of the R groups may be nitroso or nitro as described in the aforementioned patents, but preferably the R group is amino. Also, it has been found that the pADPRT inhibitory activity is strongly exhibited when the iodo moiety is adjacent to the amino moiety. In any event, the compounds to be used in the methods of the invention should have pADPRT inhibitory activity.

The compounds may be used as is, or preferably in combination with a pharmaceutically acceptable acid addition salt or other suitable pharmaceutical carrier known in the art.

DESCRIPTION OF THE PREFERRED EMBODIMENTS OF THE INVENTION

Definitions

Figure 1A:
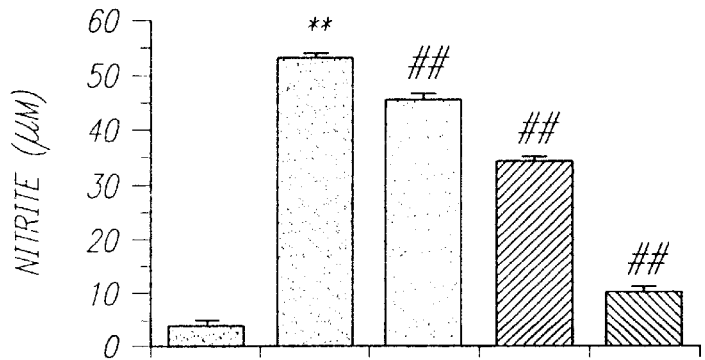
FIG. 1. Effect of $INH_2BP$ on LPS-induced (a) nitrite production, (b) 6-keto prostaglandin F1α production, (c) TNF production and (d) suppression of mitochondrial respiration in J774 cells. TNF was measured at 4 h, all other parameters at 24 h after LPS. **represents a significant change in response to LPS when compared to controls (p<0.01)m ##represents significant effect of $INH_2BP$ in the presence of LPS when compared to LPS alone (p<0.01); n=6–12 wells.
Figure 1B:
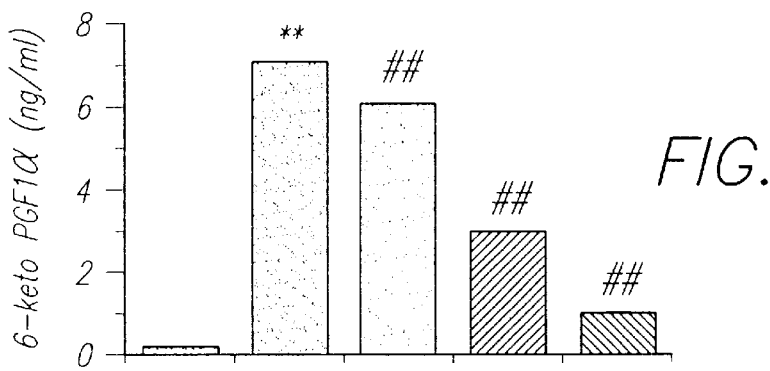
Figure 1C:
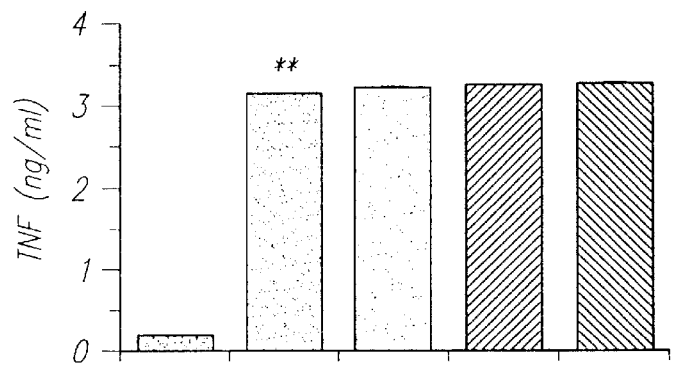
Figure 1D:
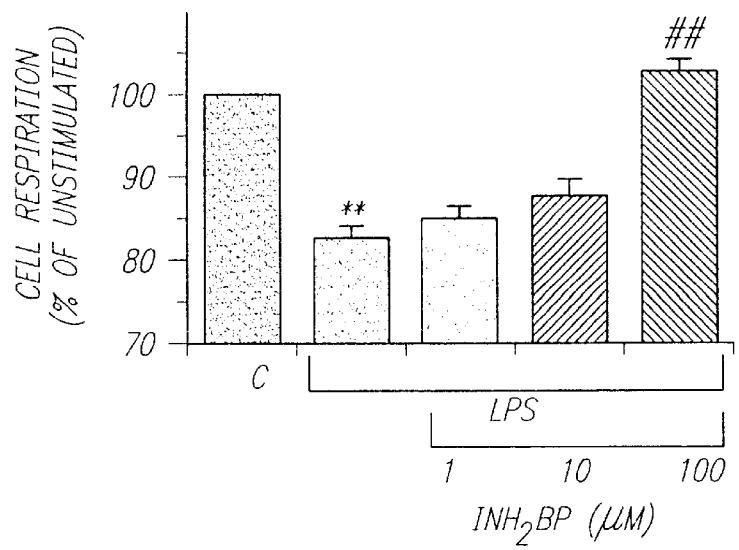

As used herein:

"Anti-inflammatory" diseases refers to diseases or conditions where there is an inflammation of the body tissue. Such diseaes include for example, Chron's disease, Barrett's disease, arthritis, multiple scelorsis, cardiomyopathic disease, colitis, infectious meningitis, encephalitis, and the like.

"Pharmaceutically acceptable acid addition salt" refers to those salts which retain the biological effectiveness and properties of the free bases and which are obtained by reaction with inorganic acids such as hydrochloric acid, hydrobromic acid, sulfuric acid, nitric acid, phosphoric acid, methanesulfonic acid, salicylic acid and the like.

"ADPRT" refers to adenosinediphosphoribose transferase and is also known as poly(ADP-ribose)polymerase (EC 2.4.99), a specific DNA-binding nuclear protein of eucaryotes that catalyzes the polymerization of ADP-ribose. The enzymatic process is dependent on DNA.

"Alkyl" refers to saturated or unsaturated branched or straight chain hydrocarbon radical. Typical alkyl groups include methyl, ethyl, propyl, isopropyl, butyl, isobutyl, tertiary butyl, pentyl, hexyl and the like.

"Alkoxy" refers to the radical —O-alkyl. Typical alkoxy radicals are methoxy, ethoxy, propoxy, butoxy and pentoxy and the like.

"Cycloalkyl" refers to saturated monocyclic hydrocarbon radical containing 3–8 carbon atoms such as cycloproply, cyclobutyl, cyclopentyl, cyclohexyl, cycloheptyl, cyclooctyl, and the like.

"Substituted phenyl" refers to all possible isomeric phenyl radicals such as mono or disubstituted with a substituent selected from the group consisting of alkyl, alkoxy, hydroxy, or halo.

"Halo" refers to chloro, fluoro, bromo or iodo, and preferably iodo.

The pADPRT inhibitory compounds of the invention (notably compounds defined above as compounds I, II or III) are potent, specific and non-toxic anti-inflammatory compounds, that can be used for conditions and diseases typically known for inflammation, such as arthritis, Chron's disease, Barrett's disease, and the like. Also, these compounds are useful in the treatment of conditions associated with gram negative and gram positive induced infections, especially those associated with gram negative infections, and including conditions associated with lipopolysaccharide condition and sepis. The compounds are especially useful in that they have very low, if any toxicity.

In practice, the compounds of the invention or their pharmaceutically acceptable salts, will be administered in amounts which will be sufficient to inhibit inflammatory conditions or disease and/or prevent the development of inflammation or inflammatory disease in animals or mammals, and be used in the pharmaceautical form most suitable for such purposes.

Administration of the active compounds and salts described herein can be via any of the accepted modes of administration for therapeutic agents. These methods include systemic or local administration such as oral, parenteral, transdermal, subcutaneous, or topical administration modes. The preferred method of administration of these drugs is oral. In some instances it may be necessary to administer the composition in other parenteral form.

Depending on the intended mode, the compositions may be in the solid, semi-solid or liquid dosage form, such as, for example, injectables, tablets, suppositories, pills, time-release capsules, powders, liquids, suspensions, or the like, preferably in unit dosages. The compositions will include an effective amount of active pADPRT inhibitory compound or the pharmaceutically acceptable salt thereof, and in addition, it may include any conventional pharmaceutical excipients and other medicinal or pharmaceutical drugs or agents, carriers, adjuvants, diluents, etc., as customary in the pharmaceutical sciences.

For solid compositions such excipients include pharmaceutical grades of mannitol, lactose, starch, magnesium stearate, sodium saccharin, talcum, cellulose, glucose, sucrose, magnesium carbonate, and the like may be used. The active pADPRT inhibitory compound defined above, may be also formulated as suppositories using for example, polyalkylene glycols, for example, propylene glycol, as the carrier.

Liquid, particularly injectable compositions can, for example, be prepared by dissolving, dispersing, etc. the active compound in a pharmaceutical solution such as, for example, water, saline, aqueous dextrose, glycerol, ethanol, and the like, to thereby form the injectable solution or suspension.

If desired, the pharmaceutical composition to be administered may also contain minor amounts of nontoxic auxiliary substances such as wetting or emulsifying agents, pH buffering agents, and other substances such as for example, sodium acetate, triethanolamine oleate, etc.

Also, if desired, the pharmaceutical composition to be administered may contain liposomal formulations comprising a phospholipid, a negatively charged phopholipid and a compound selected from cholesterol, a fatty acid ester of cholesterol or an unsaturated fatty acid. Typical neutral phospolipids include L-a-phophalidycholine, L-a-phosphatidylinosotol, L-a-phosphatidyl-serine, L-a-phosphatidylinosotol, L-a-phosphatidic acid, L-a-phosphatidylglycerol, L-a-lysophosphatidylcholine, sphingomycelin, and cardiolipin.

Typical negatively charged phospholipids include diacetyl phosphate or phosphodiglyceride, e.g., dilauroyl, dimyristoyl phosphate, dipalmitoyl phosphate, disteroyl phosphate.

Typical cholesterols and cholesterol ethers include cholesterol, 3S-hydroxy-5-cholestene, polyoxyethanylcholesteryl sebacate, cholesterol-5,6-epoxide, cholesteryl acetate, cholesteryl n-butyl ether, cholesteryl caprate, cholesteryl dodecanoate, cholesteryl ethyl ether, cholesteryl heptadecanoate, cholesteryl methyl ester.

Typical unsaturated fatty acids include arachidonic acid, docosahexanoic acid, elaidic acid, erucic acid, linoleic acid, linolenic acid, nervonic acid, oleic acid, palmitoleic acid, petroselinic acid. The halo nitro compounds may be encapsulated or partitioned in a bilayer of liposomes of the liposomal formulation according to patent application Ser. No. 08/020,035 entitled "Liposomal Formulations and Methods of Making and Using Same" filed on Feb. 19, 1993 which is incorporated herein by reference.

In the first embodiment, the liposomes are formed first and then the C-amino, nitroso or nitro compound is added. Rather than be encapsulated, the C-amino, nitroso or nitro compound partitions (locates itself) into the lipid bilayer of the liposome. To make this composition, typically, the ingredients, e.g., phosphatidyl choline, dicetyl phosphate and cholesterol are blended with a solvent such as chloroform. After blending the chloroform is driven off. Then water is added to it. When the water is added to the liposomes, it makes a multilamellar liposome (i.e., the liposomes are similar to an onion skin having many layers). The next step is to freeze and thaw them. They are frozen down rapidly in liquid nitrogen. The purpose of the rapid freeze and thaw it to make the liposome size more uniform. The liposomes at this point are varied in size and you treat and that it one or more, typically, five, times. Thawing occurs in a 37 degree water bath. Before the freeze and thaw one sonicares the mixture. The combination of sonication and thawing reduces the number of skins. The goal is to produce a unilamellar system. At this point, the C-nitroso compound is added to get a 10 millimolar (Mn) concentration. The concentration can be in excess of 15 millimolar. For this concentration of lipids, for a 60 milliliter batch, the total lipid concentration is 648 mg and 60- milliliters of water is added to that. The phosphatidyl choline is 500 mg, the cholesterol is 36 mg; the dicetyl phosphate is 112 mg.

Increasing the liposome concentration of the mixture permits it to contain more C-amino, nitroso or nitro compound. For example, it could be twice as concentrated as it is in the above mixture. For a 60 mil batch, one could double the numbers above to have 1000 mg of phosphatidyl choline, 224 mg of dicetyl phosphate and 72 mg of cholesterol. Decreasing the concentration decreases the amount of C-nitroso compound to get in there. For the hypothetical 60 milliliter batch, the upper limit of C-amino compound approaches is 15 millimolar concentration of C-amino compound. For 3-Nitrosobenzamide this is 135 mg. for a 60 milliliter batch.

The next step is to rehydrate. Then, the next step of the process is extrusion using an extruder device (Lipex Biomembranes, Inc., Vancouver, British Columbia, Canada).

The extrusion process serves two purposes; 1) making the size of the liposomes uniform; and 2) sterilization. Extrusion typically involves filtration through a j0.1 micron filter and is generally followed by freeze drying the mixture to lyophilize the mixture (takes the water out of it and makes it a fine powder). This improves solubility so that one can put up to about a 40 millimolar solution which is about three times as concentrated as prior to free drying. Freeze drying produces a mixture of powdered lipids and the powdered C-amino compound. Now one can use the same amount of the C-amino compound and a smaller amount of liquid making a more concentrated mixture. For example, one may have the same weight of C-amino, nitroso or nitro compound but have up to one-third of the original volume.

One could modify steps of the above process by, for example, eliminating steps such as freeze drying.

This process of the first embodiment does not significantly encapsulate the C-amino, nitroso or nitro compound. Instead of having the compound in the middle of the liposome the compound resides in the membrane itself. The C-amino, nitroso or nitro compound partitioned within the membrane of the liposome will migrate to the target cells and the lipid will carry the C-amino, nitroso or nitro compound into the cell membranes.

Preferably this process makes liposomes having about 0.05–0.45, and more preferably about I0.1–0.2 micron, diameter. Unilamellar or multilamellar liposomes are effective.

The second purpose of extrusion is to sterilize the mixture. To sterilize, the liposomes are generally made smaller than 45 microns in diameter. Sizes less than 0.05 microns would theoretically work. The process of the first embodiment has the advantage that, for example, in water 3NOBA only has a 0.5 millimolar concentration. The present liposomal composition achieves concentrations of 15 millimolar.

Moreover, unlike 3-NOBA merely in aqueous solution, the NOBA-containing liposomal solution is resistant to ascorbic acid. This makes it useful in laboratory mice experiments. The solution may contain the NOBA monomer or NOBA dimer.

In a second embodiment one may start with a film of the lipid components, hydrate the film with an aqueous solution of drug. This automatically forms lipids which entrap (encapsulate) the drug. This occurs with compounds which are liposome membrane impermeable. An example of such compounds are those in U.S. Pat. No. 5,262,564, issued Nov. 16, 1993, e.g., L-cystine sulfinic adducts of 3-NOBA.

Parental injectable administration is generally used for subcutaneous, intramuscular or intravenous injections and infusions. Injectables can be prepared in conventional forms, either as liquid solutions or suspensions or solid forms suitable for dissolving in liquid prior to injection.

A more recently devised approach for parenteral administration employs the implantation of a slow-release or sustained-released systems, which assures that a constant level of dosage is maintained, according to U.S. Pat. No. 3,710,795, which is incorporated herein by reference.

Any of the above pharmaceutical compositions may contain 0.1–99%, preferably 1–70% of the active pADPRT inhibitory compounds, especially the halo- C-amino, nitroso or nitro compounds of the formulae I, II or III, above as active ingredients.

Chronic inflammation is known to facilitate carcinogenic transformation in various tissues. 5-iodo-6-amino-1,2-benzopyrone ($INH_2BP$), a novel inhibitor of the nuclear enzyme poly-ADP ribose polymerase (pADPRT) has recently been shown to regulate a variety of cellular signal transduction pathways and to abrogate in vivo tumorigenicity by a Ha-ras transfected endothelial cell line. As one aspect of the present invention demonstrates the effect of pADPRT inhibitory compounds such as $INH_2BP$ on the activation by endotoxin (bacterial lipopolysaccharide, LPS) on the production of the inflammatory mediators tumor necrosis factor alpha (TNF), interleukin-10 (IL-10) and interleukin-6 (IL-6), nitric oxide (NO) and prostaglandins in vitro and in vivo. In addition, the present invention shows the effect of pADPRT inhibitory compounds such as $INH_2BP$ on the activation of mitogen-activated protein kinase (MAP kinase) and nuclear factor kB (NF-kB) in vitro. In cultured J774 and RAW 264.7 macrophages, LPS induced the production of prostaglandin metabolites, the release of TNF and the expression of the inducible isoform of NO synthase (iNOS). The production of prostaglandins and of NO were inhibited by $INH_2BP$ in a dose-dependent manner, while the short-term release of TNF-alpha was unaffected. $INH_2BP$ markedly suppressed LPS-mediated luciferase activity in RAW cells transiently transfected with a full length (−1592 bp) murine macrophage iNOS promoter-luciferase construct, but not in a deletional construct consisting of −367 bp. In vivo, $INH_2BP$ pretreatment inhibited the induction of iNOS by LPS in rats, did not affect the LPS-induced TNF and IL-6 response, but enhanced LPS-induced IL-10 production. $INH_2BP$ pretreatment markedly improved the survival of mice in a lethal model of endotoxin shock. These results demonstrate that pADPRT inhibitory compounds such as $INH_2BP$ have potent antiinflammatory action in vitro and in vivo.

Poly-ADP ribose synthetase (PARS) is a nuclear enzyme activated by DNA single strand breaks. Massive activation of PARS, in response to hydrogen peroxide- peroxynitrite- or ionizing radiation-induced extensive DNA single strand breakage can initiate an energy-depleting futile cycle culminating in cellular injury. The production of peroxynitrite has recently been demonstrated in various forms of inflammation, including arthritis and carrageenan-induced paw edema. The present invention shows the effect of the novel, potent inhibitor of PARS, pADPRT inhibitory compounds such as 5-iodo-6-ammino-1,2-benzopyrone ($INH_2BP$), in a rat model of carrageenan-induced paw edema and in a mouse model of collagen-induced paw edema at 1–4 h. Collagen-induced arthritis was induced in male DMA/1J mice, with two injections of type II collagen at Day 1 and Day 21. Oral treatment of mice with $INH_2BP$ (0.5 g/kg, daily), starting at the onset of arthritis (Day 25), delayed the development of the clinical signs of arthritis at Days 26–35. $INH_2BP$ treated animals exhibited a reduced arthritic index (arthritic score: 20–50% of the score seen in the vehicle-treated mice), and improved histological status, as examined in the knee and paw. These data demonstrate that the PARS inhibitor $INH_2BP$ exhibits antiinflammatory effects in vivo $INH_2BP$, even with a relatively late start of administration, was able to delay the course of the collagen-induced arthritis. The data of the invention support the view that PARS activation plays a role in the development of arthritis, and possibly, other forms of inflammation and inflammatory diseases.

The following examples serve to illustrate the invention. They should not be construed as narrowing it, or limiting its scope.

EXAMPLE 1

Cell Culture

The mouse macrophage cell lines J774 and RAW 264.7 were cultured in Dulbecco's modified Eagle's medium (DMEM) as described; Szabo et al., 1996, "DNA strand breakage, activation of poly-ADP ribosyl synthetase, and cellular energy depletion are involved in the cytotoxicity in macrophages and smooth muscle cells exposed to peroxynitrite," Proc. Natl. Acad. Sci. U.S.A. 93:1753–1758; Zingarelli et al., 1996, "Peroxynitrite-mediated DNA strand breakage activates poly-ADP ribosyl synthetase and causes cellular energy depletion in macrophages stimulated with bacterial lipopolysaccaride," J. Immunol. 156:350–358. In separate studies, peritoneal macrophages were obtained from male Wistar rats and cultured in vitro for 24 hours in the absence or presence of LPS and with or without $INH_2BP$. Rats were sacrificed and peritoneal macrophages taken and cultured in DMEM. Cells were treated with E. Coli LPS (10 mg/ml) or LPS and INF (50 u/ML) for various times, in the presence or absence of various concentrations (1–150 mM) $INH_2BP$ or other pharmacological inhibitors.

MAP Kinase Related Assays

Raw cells were washed in PBS and collected and lysed using 100 ml of lysis buffer per million cells. (50 mM Tris-HCl pH 7.4, 1% NP-40, 0.4 M NaCl, 0.1 mM $NaVO_3$, 50 mM KF, 1 mM EGTA, 2 mM PMSF, 25 nM okadaic acid, 1 mg/mL of each leupeptin, aprotinine, arnastatine and antipaine). Lysis was carried out for 20 minutes on ice followed by a 14 min. centrifugation at 13000 rpm in an Eppendorf centrifuge. Supernatants were saved and their protein content were assayed using the Bio-Rad dye assay.

In Gel MAP Kinase Assay

Protein samples (50 mg/lane) were electrophoresed in a 10% SDS-PAGE gel containing immobilized myelin basic protein (MBP, 250 mg/mL gel). After electrophoresis, the gel was washed once with 50 mM TRIS-HCI pH 7.7 buffer (25 mL, 20 min.), followed by two 30 min. incubations with the same buffer containing 25% i-propanol. The gel was then washed once with the Tris-Hcl buffer and soaked into a solution of 50 mM Tris-HCl pH 7.7, mM 2-mercaptoethanol, 5 M guanidine hydrochloride (50 mL) for an hour, changing the incubating solution at 30 min. The proteins were then renurtured by incubating the gel in five changes of a solution of 50 mM TRIS-HCL Ph 7.7, Mm 2-mercaptoethanol, 0.04% NP-40 over a 16 hours period of time. The gel was then washed twice and preincubated for half an hour in a solution containing 50 mM TRIS-HCl pH 7.7, 5 mM $MgCl_2$ 7 mm 2-mercaptoethanol. The final incubation was carried out in the same solution supplemented with 10 mm of $^{32}P$-g] ATP (50 mCi/assay) for an hour. At the end of the incubation, the gel was washed free of unbound radioactivity using 3×25 mL of 10% TCA and 3×25 ml of 10% acetic acid, dried and autoradiographed; Sasaki et al., 1995, "Permissive effect of ceramide on growth factor-induced cell proliferation," Biochem. J. 311:829–34.

MAP Kinase Western Blotting

One hundred mg of cell extract proteins were loaded onto a 10% SDS-PAGE gel, electrophoresed, transblotted onto nitrocellulose membrane and immunoprobed. The first antibody (anti-MAP kinase) was from UBI, the second antibody was alkaline phosphatase labeled and from NEN Biolabs. Detection was by enhanced chemiluminesence; Bauer et al., 1995, "Modification of growth related enzymatic pathways and apparent loss of tumorigenicity of a ras-transformed bovine endothelial cell line by treatment with 5-iodo-6-amino-1,2-benzopyrone ($INH_2BP$)," Int. J. Oncol. 8:239–252.

Preparation of Nuclear Extracts and NF-kB Western Blotting

Cells were treated with LPS in the presence and absence of $INH_2BP$ for 90 minutes. Mininuclear extracts were prepared as described; Hassanain et al., 1993, "Enhanced gel mobility shift assay for DNA-binding factors," Anal. Biochem. 213:162–7. Briefly, cells were scraped, briefly centrifuged and pellets resuspended in 400 ml cold Buffer A [Hepes pH 7.9 (10 mM), KCl (10 mM), EDTA (0.1 mM), EGTA (0.1 mM), DTT (1 mM), PMSF (0.5 mM), pepstatin A (1 mg/ml), leupeptin (10 mg/ml), and aprotinin (10 mg/ml)], on ice for 15 minutes, in the presence of 25 ml 1% NP-40. Then, samples were vortexed, centrifuged for 1 minute at 10,000 g, and the pellet resuspended with 100 ml Buffer B {Hepes pH 7.9 (20 mM), NaCl (400 mM), EDTA (1 mM), EGTA (1 mM), DTT (1 mM), PMSF (0.5 mM), pepstatin A (mg/ml), leupeptin (10 mg/ml) and aprotinin (10 mg/ml)]. After shaking on a rocker platform for 15 minutes at 4° C., samples were centrifuged for 15 minutes 15 100,000 g at 4° C. 70 ml aliquots were then treated with 150 ml SDS-PAGE sample buffer. Western blotting was performed as described above, with rabbit anti-mouse NF-kB primary antibody (Santa Cruz Biotechnology, Santa Cruz, Calif.) 1:750 in Tween TBS (0.02%).

Measurement of Nitrite or Nitrite/nitrate Concentration

Nitrite in culture supernatants at 24 hours after stimulation was measured as described; Szabo et al., 1996, "DNA strand breakage, activation of poly-ADP ribosyl synthetase, and cellular energy depletion are involved in the cytotoxicity in macrophages and smooth muscle cells exposed to peroxynitrite," Proc. Natl. Acad. Sci. U.S.A. 93:1753–1758; Zingarelli et al., 1996, "Peroxynitrite-mediated DNA strand breakage activates poly-ADP ribosyl synthetase and causes cellular energy depletion in macrophages stimulated with bacterial lipopolysaccharide," J. Immunol. 156:350–358; Szabo et al., 1994, "Spermine inhibits the production of nitric oxide in immuno-stimulated J774.2 macrophages: requirement of a serum factor," Br. J. Pharmacol. 112:355–356; by adding 100 ml of Griess reagent (1% sulfanilamide and 0.1% naphthylenediamide in 5% phosphoric acid) to 100 ml samples of medium. The optical density at 550 nm (OD $_{550}$) was measured using a Spectramax 250 microplate reader (molecular Devices, Sunnyvale, Calif.). For the determination of total nitrite/nitrate concentrations in plasma samples, nitrate was reduced to nitrite by incubation with nitrate reductase; Zingarelli et al., 1996, "Peroxynitrite-mediated DNA strand breakage activates poly-ADP ribosyl synthetase and causes cellular energy depletion in macrophages stimulated with bacterial lipopolysaccharide," J. Immunol. 156:350–358.

Measurement of 6-Keto Prostaglandin $F_{1a}$ 6-keto prostaglandin $F_{1a}$ production at 4 hours after LPS stimulation was measured in 100 ml samples of cell culture supernatant using a specific radioimmunoassay; Szabo et al., 1994, "Spermine inhibits the production of nitric oxide in immuno-stimulated J774.2 macrophages: requirement of a serum factor," Br. J. Pharmacol. 112:355–356.

Cytokine Measurements

Cytokine levels in plasma and cell culture supernatants were determined by ELISA. Plasma levels of IL-10 and IL-6 were measured using ELISA kits from Endogen (Endogen Inc., Boston, Mass.). Concentrations of TNF-α in the plasma and cell culture supernatants were determined using ELISA kits from Genzyme (Genzyme Corp., Boston, Mass.) as described; Szabo et al., 1997, "Isoproterenal regulates tumour necrosis factor, interleukin-10, interleukin-6 and nitric oxide production and protects against the development of vascular hyporeactivity in endotoxemia," Immunology 90:95–100.

Measurement of Mitochondrial Respiration

Mitochondrial respiration at 24 hours was assessed by the mitochondrial-dependent reduction of 3-(4,5-dimethylthiazol-2-yl)-2,5-diphenyltetrazolium bromide to formazan; Szabo et al., 1996, "DNA strand breakage, activation of poly-ADP ribosyl synthetase, and cellular energy depletion are involved in the cytotoxicity in macrophages and smooth muscle cells exposed to peroxynitrite," Proc. Natl. Acad. Sci. U.S.A. 93:1753–1758; Zingarelli et al., 1996, "Peroxynitrite-mediated DNA strand breakage activates poly-ADP ribosyl synthetase and causes cellular energy depletion in macrophages stimulated with bacterial lipopolysaccharide," J. Immunol. 156:350–358.

Northern Blotting for iNOS mRNA

After exposing cells to LPS in the presence or absence of $INH_2BP$ for 4 hours, total RNA was extracted as described using TRIZOL. Aliquots containing 15 mg total RNA underwent electrophoresis on a 1% agarose gel containing 3% formaldehyde. RNAs were blot transferred to nylon membrane and UV auto-crosslinked. Membranes were hybridized as described; Lowenstein et al., 1993, "Macrophage nitric oxide synthase gene: two upstream regions mediate induction by interferon gamma and lipopolysaccharide," Proc. Natl. Acad. Sci. U.S.A. 90:9730–9734; overnight at 42° C. with a murine iNOS cDNA probe ($10^6$ .cpm/ml) labeled with [$^{32}$P]dCTP (specific activity, 3,000 Ci/mM; NEN) by random priming (Pharmacia, Piscataway, N.J.). The hybridized filters were serially washed at 53° C. using 2X sodium citrate, sodium chloride, 0.1% SDS and 25 mM NaHP04, 1 mM EDTA, 0.1% SDS solutions. After probing for iNOS, membranes were stripped with boiling 5 mM EDTA and rehybridized with a [$^{32}$P]-radiolabeled oligonucleotide probe for 18S ribosomal RNA as a housekeeping gene. After washing, exposure was carried out overnight using a Phosphor Imager screen.

iNOS Western Blotting

Cells were treated with LPS in the presence and absence of pADPRT inhibitor for 20 hours. Cells were then scraped in cold PBS and centrifuged at 14000 g for 30 seconds. The supernatant was removed and lysis buffer containing RIPA (500 mL), aprotin (10 mg/ml), and PMSF (0.5 mM) was added. DNA was sheered by passing samples through a 22 gauge needle. Protein content was determined by the Bradford method (BIO-Rad). Cytosolic protein (200 mg/lane) was added to SDS-PAGE buffer, boiled for 5 minutes, separated with 7.5% SDS-PAGE, and transferred to nitrocellulose membranes (0.2 mm) using a Semi-Dry method with an isotachophoretic buffer system. After 1 hour blocking in 3% gelatin and subsequent washing, the samples were immunoblotted in Tween Tris Buffered Saline (TTBS) and 1% gelatin, with primary rabbit anti-mouse iNOS (upstate Biotechnology, Lake Placid, N.Y.) 1:1000 in TTBS (0.0%) for 2.5 hours. An alkaline phosphatase-conjugated goat anti-rabbit iGG antibody was used as secondary antibody. Antibody binding was visualized by nitrobule tetrazolium/5-bromo-4-chloro indolyl phosphate (NBT/BCIP) in carbonate buffer (BIO-RAD).

Measurement of iNOS Activity

Cells were treated with LPS in the presence and absence of pADPRT inhibitor for 12 hours. The measurement of the calcium-independent conversion of 1-arginine to L-citrulline in homogenates of the J774 cells or in lung homogenates was used as an indicator of iNOS activity as described; Szabo et al., 1994, "Spermine inhibits the production of nitric oxide in immuno-stimulated J774.2 macrophages: requirement of a serum factor," Br. J. Pharmacol. 112:355–356. Cells were scraped or lungs were put into a homogenation buffer composed of: 50 mM Tris HCl, 0.1 mM EDTA, 0.1 mM EGTA and 1 mM phenylmethylsulfonyl fluoride (pH 7.4) and homogenized in the buffer on ice using a Tissue Tearor 985-370 homogenizer (Biospec Products, Racine, Wis.). Conversion of [$^3$H]-L-arginine to [$^3$H]-L-citrulline was then measured in the homogenates. Homogenates (30 ml) was incubated in the presence of [$^3$H]-L-arginine (10 mM, 5 kBq/tube), NADPH (1 mM), calmodulin (30 nM), tetrahydrobiopterin (5 mM) and EGTA 5 mM) for 20 minutes at 22° C. Reactions were stopped by dilution with 0.5 ml of ice cold HEPES buffer (pH 5.5) containing EGTA 2 mM) and EDTA (2 mM). Reaction mixtures were applied to Dowex 50W (Na+ form) columns and the eluted [$^3$H]-L-citulline activity was measured by scintillation counting.

Functional Assay of iNOS Promotor

Since under our experimental conditions, J774 cells were resistant to our attempts to transiently transfect them using the calcium phosphate, lipofectin, and lipofectamin methods, transfection studies were performed in RAW 264.7 cells. iNOS promoter activity was evaluated by transient transfection of RAW 264.7 cells with reporter gene constructs incorporating the 5' murine macrophage iNOS promoter region upstream from the reporter gene luciferase; Lowenstein et al., 1993, "Macrophage nitric oxide synthase gene: two upstream regions mediate induction by interferon gamma and lipopolysaccharide," $Proc.$ $Natl.$ $Acad.$ $Sci.$ $U.S.A.$ 90:9730–9734; (kindly provided by Dr. Charles J. Lowenstein, Johns Hopkins University). Two constructs were used: a full length promoter construct (−1592 bp) and a deletional construct consisting of −367 bp. Cells were plated into 6-well culture plates at −50% confluence and transfected with the respective iNOS promoter-luciferase construct in equimolar amounts using cationic liposomes (Lipofectin, Gibco). In order to control for differences in transfection efficiencies, cells were co-transfected with pSV40-b-galactosidase. After transfection, cells were allowed to recover overnight, then subsequently treated with media alone (control), LPS (10 mg/ml), or LPS plus $INH_2BP$ (100 mM). After 4 hours of treatment, cells were washed once in PBS, lysed in reporter lysis buffer (Promega), and analyzed for luciferase activity was corrected for respective raw-galactosidase activity and is expressed as fold increase over control cells (transfected and treated with media alone).

In vivo Experiments

Male Wistar rats and Male BALB/c mice were obtained from Charles River Laboratories (Wilmington, Mass. or Budapest, Hungary). Animals received food and water ad libitum, and lighting was maintained on 12 hour cycle. Rats were injected i.p. with $E.$ $coli$ LPS (15 mg/kg) and sacrificed at 6 hours. Plasma samples were taken for nitrite/nitrate determinations and lung samples for iNOS measurements. Separate groups of rats were treated with $INH_2BP$ (10 mg/kg i.p.) 10 minutes prior to LPS or 2 hours after LPS injection.

In studies for the measurement of LPS-induced cytokine response, mice were injected i.p. with either drug vehicle, or with $INH_2BP$ (10 mg/kg) in a volume of 0.1 ml/10 g body weight. Half an hour later they were challenged with 4 mg/kg of i.p. LPS. The animals were killed at 90 minutes after LPS treatment, blood was collected in ice-cold Eppendorf tubes containing EDTA, and centrifuged for 10 minutes at 4° C. The plasma was stored at −7° C. until assayed.

In survival studies with mice, animals were subjected to i.p. injection of LPS (120 mg/kg) at time 0 and survival was monitored for 42 hours after LPS. Separate groups of mice received vehicle or $INH_2BP$ treatment (0.1–10 mg/kg i.p.) at times −18 hours, −4 hours, 0 hours, 6 hours, 24 hours and 30 hours relative to LPS.

Materials

DMEM, RPM1, TRIZOL and fetal calf serum were from Gibco (Grand Island, N.Y.). [$^3$H]NAD+ and [$^{32}$P]NAD$^+$ were obtained from DuPont NEN (Boston, Mass.). Alcohol dehydrogenase and ND$^+$ were obtained from Boehringer Mannheim (Indianapolis, Ind.). PD 98059 was obtained from Cal biochem (La Jolla, Calif.). All other drugs were obtained from Sigma (St. Louis, Mo.).

Statistical Evaluation

All values in the figures and text are expressed as mean±standard error of the mean (S.E.M.) of n observations ($n \geq 4$). Student's unpaired t-test was used to compare means between groups. A p-value less than 0.05 was considered statistically significant.

Figure 2A:
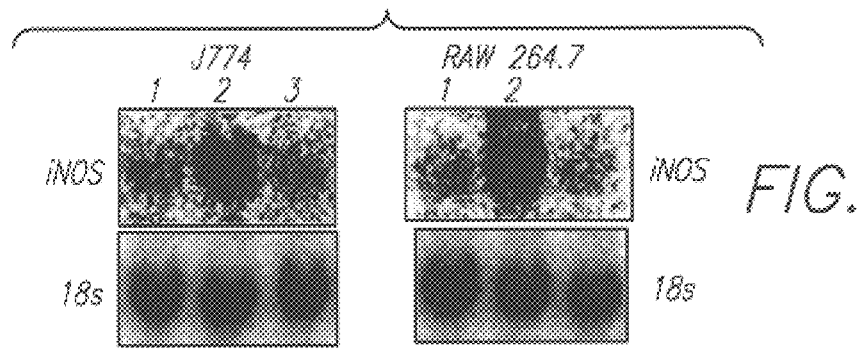
FIG. 2. $INH_2BP$ inhibits iNOS expression in J774 and RAW 264.7 cells. (a) Representative Northern blots of iNOS and 18s mRNA in J774 cells (A) and RAW 264.7 macrophages (B) under control conditions (lane 1), at 4 h after LPS treatment (lane 2) and at 4 h after LPS treatment in cells in the presence of $INH_2BP$ (100 μM) (lane 3). (b) Effect of $INH_2BP$ on iNOS activity ini the homogenates of J774 cells under control conditions (C and C+ $INH_2BP$) and at 12 h after LPS treatment (LPS and LPS+$INH_2BP$). **represents a significant effect of LPS when compared to controls (p<0.01); ##represents significant inhibition by $INH_2BP$ (p<0.01); n=4. (c) Representative iNOS Western blot in control J774 cells and in cells at 12 h after LPS in the presence or absence of $INH_2BP$.
Figure 2B:
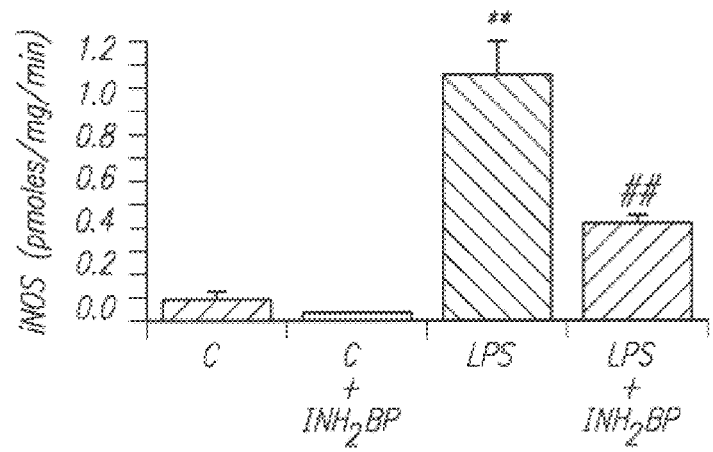
Figure 2C:
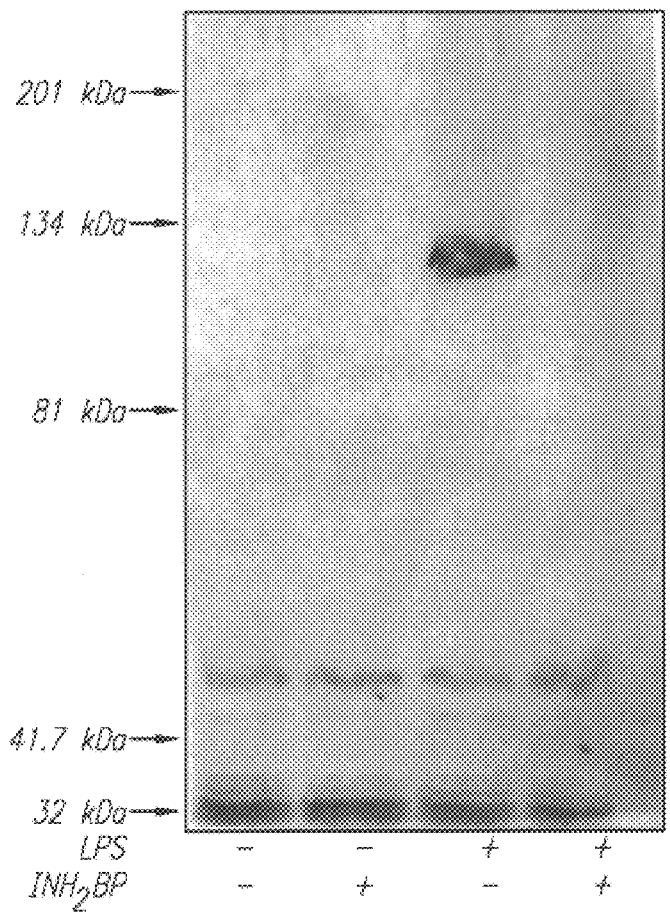
Figure 3A:
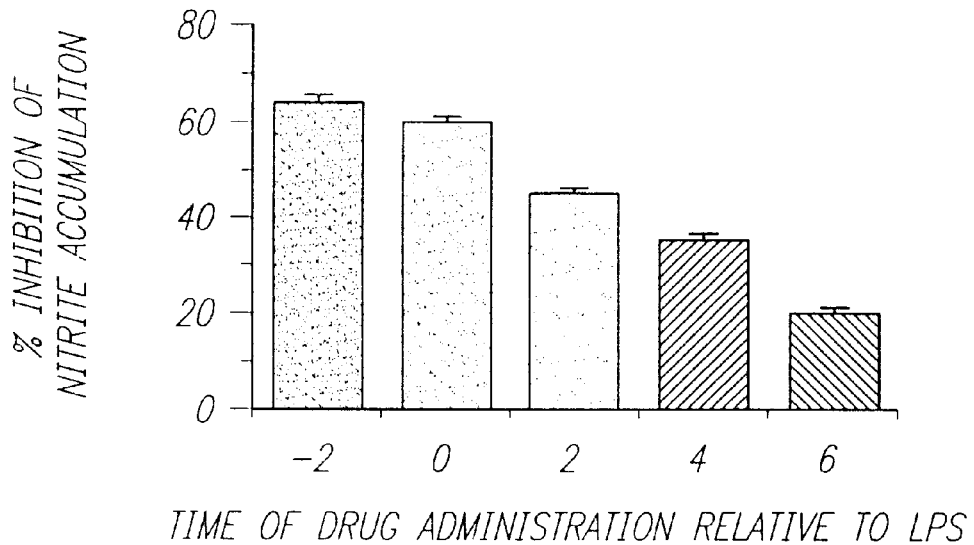
FIG. 3. (a) Time-dependent loss of the inhibition of nitrite accumulation by $INH_2BP$ (100 μM), when given at 2 h prior to LPS together with LPS or at 2, 4 and 6 h after LPS. (b) Effect of $INH_2BP$ on nitrite accumulation in J774 cells stimulated with the combination of LPS and IFN; n=6–12 wells.
Figure 3B:
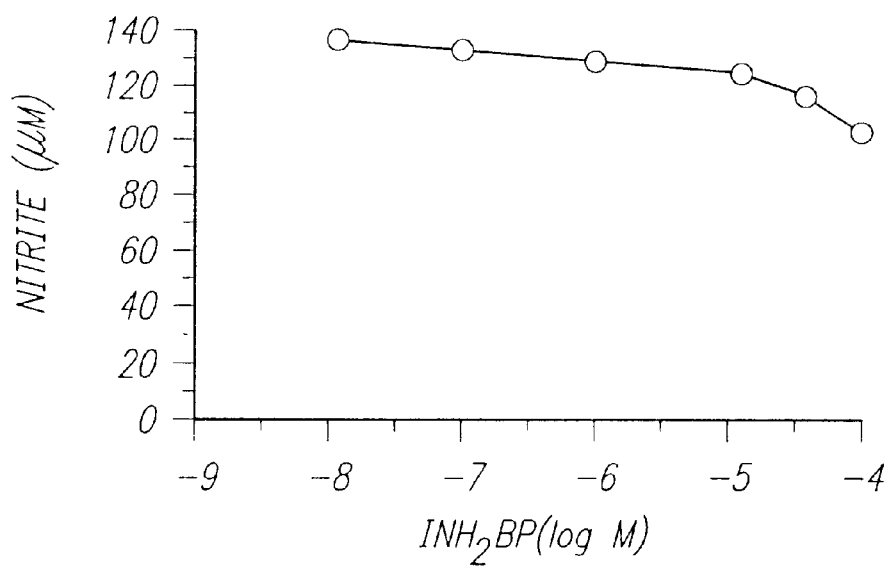

Results $INH_2BP$ suppresses LPS-induced nitric oxide and prostaglandin but no TNF-a production in J774 macrophages $INH_2BP$ treatment caused a dose-dependent inhibition of LPS-induced nitrite formation in J774 macrophages (FIG. 1$a$). Similarly, $INH_2BP$ suppressed LPS-induced production of 6-keto prostaglandin $F_{1a}$ (FIG. 1$b$), but not the production of TNF (FIG. 1$c$), and restored the LPS-induced suppression of mitochondrial respiration (FIG. 1$d$). $INH_2BP$ caused a marked inhibition of iNOS mRNA and protein expression (FIG. 2$a$–$c$). The inhibition of nitrite production by $INH_2BP$ was greatly diminished when the agent was given several hours LPS, as opposed to prior to the stimulus of iNOS induction (FIG. 3$a$). Moreover, the inhibitory effect of $INH_2BP$ on iNOS was greatly reduced when LPS was used in combination was interferon-gamma (INF-g 50 u/mL) for immunostimulation (FIG. 3$b$).

Selective regulation of the induction of the iNOS promoter by $INH_2BP$

Figure 4:
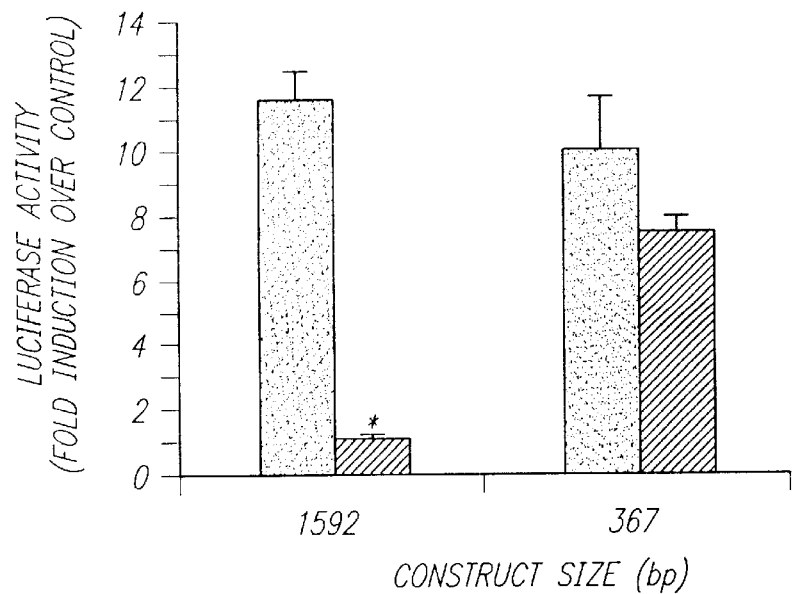
FIG. 4. Effect of $INH_2BP$ on the induction of luciferase activity by LPS in RAW 264.7 cells transiently transfected with either a full length (–1592 bp) or a deletional (–367 bp) iNOS promoter-luciferase construct. In cells transfected with either the full length or the deletional construct (black bars), treatment with LPS (10 μg/ml), 4 h) led to a 10 to 12-fold induction of luciferase activity, over control values. Co-treatment with $INH_2BP$ inhibited LPS-mediated increases in luciferase activity in cells transfected with the full length construct, but had no significant effect in cells transfected with the –367 bp deletional construct (grey bars). Data are expressed as fold increases in luciferase activity over control cells, and are corrected for respective beta-galactosidase activity. *represents significant effect of $INH_2BP$ in the presence of LPS when compared to LPS alone (p<0.05); n=4 separate transfections.

In order to further study the regulation of iNOS promoter by $INH_2BP$ we performed transient assays using murine macrophage iNOS promoter-luciferase constructs. Consistent with previous data; Lowenstein et al., 1993, "Macrophage nitric oxide synthase gene: two upstream regions mediate induction by interferon gamma and lipopolysaccharide," $Proc.$ $Natl.$ $Acad.$ $Sci.$ $U.S.A.$ 90:9730–9734, we found an important role for LPS-mediated transcriptional regulation of murine macrophage iNOS, as evidence by an −10- to 12-fold induction of luciferase activity by LPS (FIG. 4). Co-treatment of cells transfected with the full length (−1592 bp) promoter construct with $INH_2BP$, completely inhibited LPS-mediated luciferase activity (FIG. 4). However, similar co-treatment of cells transfected with the −367 bp deletional construct did not significantly affect LPS-mediated luciferase activity (FIG. 4).

Figure 5A:
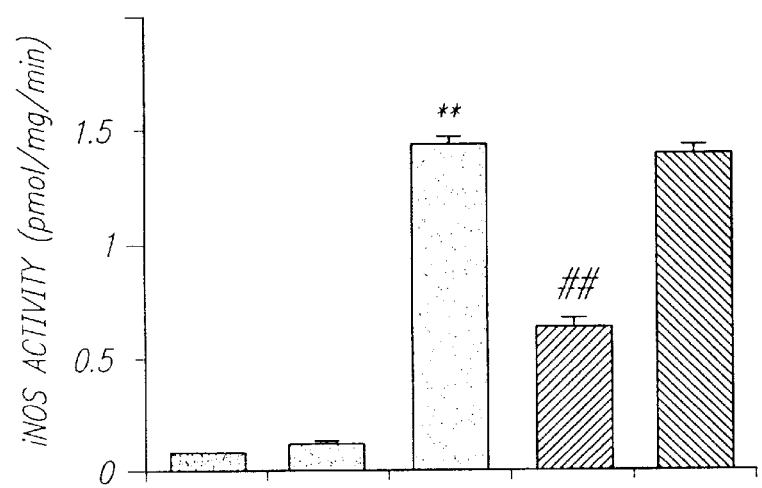
FIG. 5. $INH_2BP$ suppresses the induction of iNOS in conscious rats. iNOS activity in lung homogenates (a) and plasma nitrite-nitrate concentrations (b) in control rats (c), in rats injected with $INH_2BP$ ($INH_2BP$); in rats injected with LPS (15 mg/kg i.p. for 6 h); and the effect of treatment with $INH_2BP$ (10 mg/kg i.p.), when given 10 min. prior to LPS ($INH_2BP$+LPS) or at 2 h after LPS (LPS+$INH_2BP$). **represents a significant effect of LPS when compared to controls (p<0.01); ##represents significant inhibition by the pADPRT inhibitor (p<0.01); n=4–5.
Figure 5B:
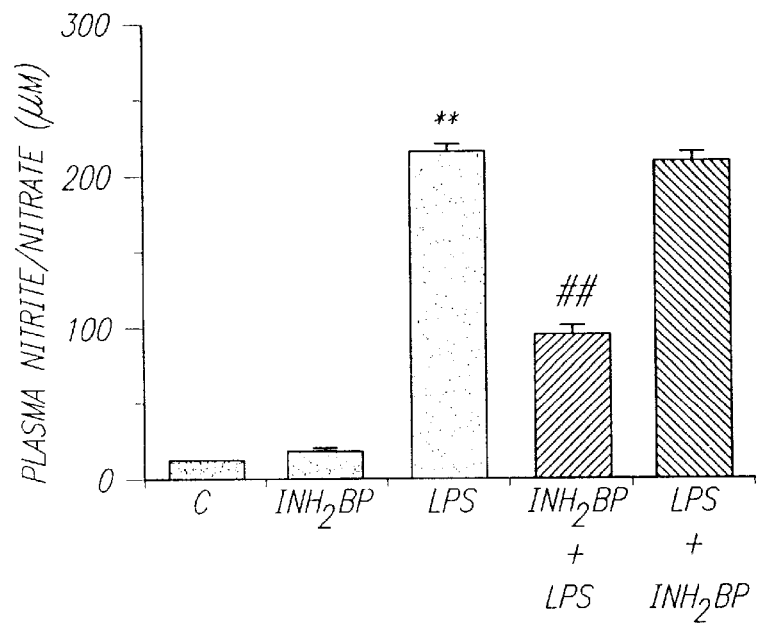

In vivo antiinflammatory effects of $INH_2BP$ $INH_2BP$ pretreatment significantly reduced the LPS-induced increase in plasma nitrite-nitrate and the increase in pulmonary iNOS activity in conscious rats (FIG. 5). The inhibitory effect of $INH_2BP$ on NO production was reduced when the agent was added to the cells or to the animals several hours after LPS stimulation (FIG. 5). Similarly to the transformed cell lines, treatment with 100 mM $INH_2BP$ significantly reduced (by 56±7%, p<0.01) nitrite production in primary cells (peritoneal macrophages obtained from rats) stimulated with LPS (10 mg/ml) in vitro (n=4).

Figure 6A:
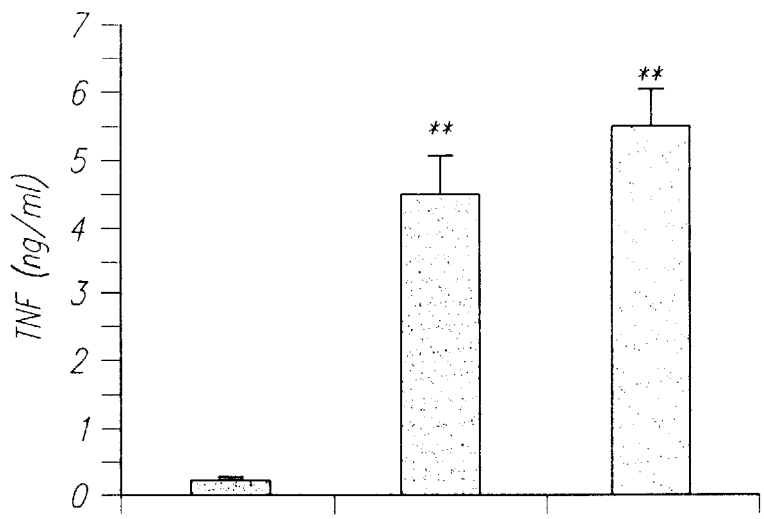
FIG. 6. Effect of $INH_2BP$ (10 mg/kg i.p.) on the LPS-induced TNF, IL-10 and IL-6 resposnes in mice, at 90 min. after LPS administration (4 mg/kg i.p.). ##represents a significant effect of LPS when compared to controls (p<0.01); ##represents significant augmentation of the response by $INH_2BP$ (p<0.01); n=4–5.
Figure 6B:
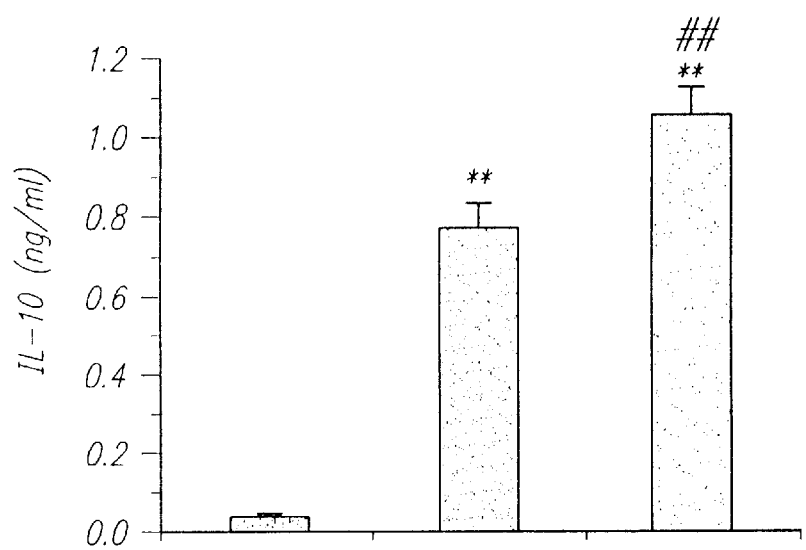
Figure 6C:
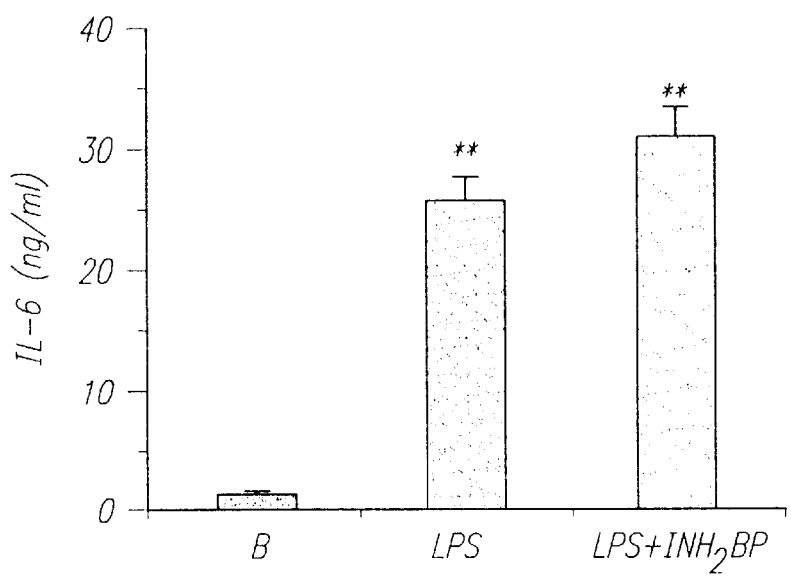

Similarly to the in vitro results (FIG. 1$c$), $INH_2BP$ did not significantly affect the LPS-induced increase in plasma TNF levels in mice (FIG. 6$a$). Nor did $INH_2BP$ affect LPS-induced IL-6 production (FIG. 6C). However, $INH_2BP$ caused an augmentation of the LPS-induced IL-10 plasma response (FIG. 6$b$).

Figure 7:
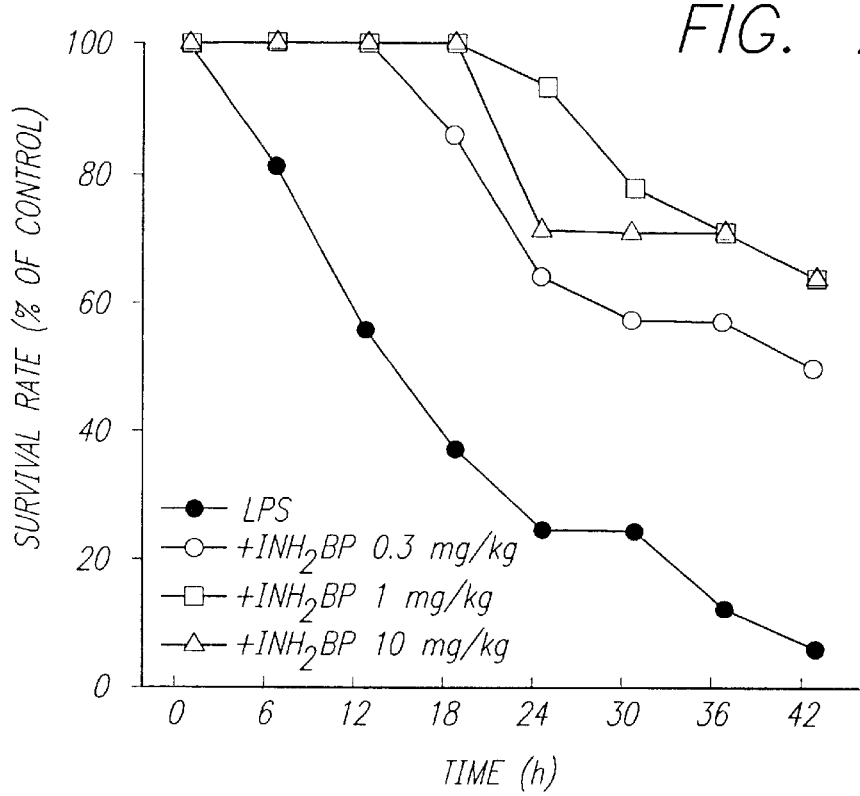
FIG. 7. $INH_2BP$ improves survival in mice subjected to endotoxin shock: effect of $INH_2BP$ pretreatment (0.3–10 mg/kg) on endotoxin-induced (120 mg/kg i.p.) mortality in mice; n=7–8 animals in each group.

Pretreatment of mice by $INH_2BP$ caused a significant and dose-dependent improvement in the survival rate subjected to lethal doses of LPS (FIG. 7).

$INH_2BP$ activity abolishes LPS-induced activation of MAP kinase but does not alter activation and nuclear translocation of NF-kB.

There are a multitude of intracellular processes which precede the induction if iNOS and the production of other inflammatory mediators. Activation of tyrosine kinases; Levitzki, A., 1994, "Signal-transduction therapy. A novel approach to disease management," $Eur.$ $J.$ $Biochem.$ 226:1–13; Novogrodsky et al., 1994, "Prevention of lipopolysaccharide-induced lethal toxicity by tyrosine kinase inhibitors," $Science$ 264 (Wash):1319–22; Marczin et al., 1993, "Tyrosine kinase inhibitors suppress endotoxinand IL-1beta-induced NO synthesis in aortic smooth muscle cells," *Am. J. Physiol.* 265:H1014–1018, mitogen-activated protein kinase (MAP kinase); Matsuda et al., 1994, "Signaling pathways mediated by the mitogen-activated protein (MAP) kinase kinase/MAP kinase cascade," *J. Leukocyte Biol.* 56:548–53; L'Allemain, G., 1994, "Deciphering the MAP kinase pathway," *Progr. Growth Factor Res.* 5:291–334; Cowley et al., 1994, "Activation of MAP kinase kinase is necessary and sufficient for PC12 differentiation and for transformation of NIH 3T3 cells.," *Cells* 77:841–52; and the NF-kB pathway; Baeuerle et al., 1994, "Function and activation of NF-kB in the immune system," *Ann. Rev. Immunol.* 12:141–79; Schreck et al., 1992, "Nuclear factor kappa B: an oxidative stress-responsive transcription factor of eukaryotic cells (a review)," *Free Radical Res. Comm.* 17:221–37; Muller et al., 1993, "Nuclear factor kappa B, a mediator of lipopolysaccharide effects," *Immunobiol.* 187:233–56; are recognized as important factors in the inflammatory mediators. We investigated, therefore, whether INH$_2$BP affects the activation of MPA kinase and the NF-kB in response to LPS stimulation in order to elucidate the potential involvement of these pathways in the inhibitory effect by INH$_2$BP of the inflammatory process.

Figure 8:
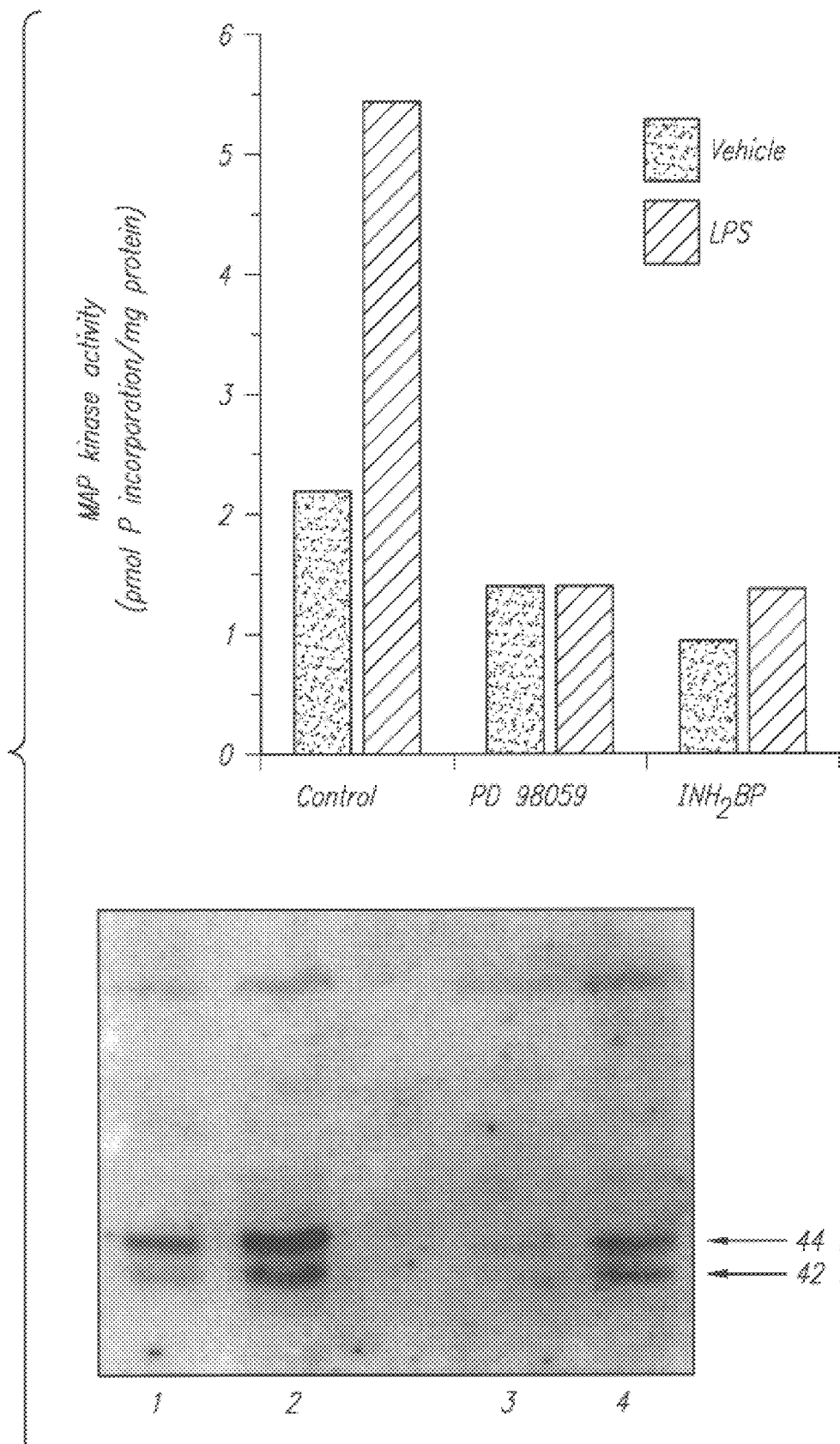
FIG. 8 (a) MAP kinase activity in RAW 264.7 cells treated with vehicle or 1PS (10 μg/ml) for 24 h ni presence or absence of 100 μM PD 98059 or 150 μM $INH_2BP$. Data represent values obtained in a typical experiment: similar results were seen on 3 different experimental days. (b) Representative in gel MAP kinase assay in RAW 264.7 cells at 24 h after vehicle or LPS treatment in the presence or absence of 150 μM $INH_2BP$. Lanes 1–4 represent the following groups, respectively: 1: vehicle-treated control; 2: LPS treatment; 3: vehicle treatment in the presence of 150 μM $INH_2BP$; 4: LPS treatment in the presence of 150 μM $INH_2BP$.

There was a significant basal MAP kinase activity in unstimulated RAW 264.7 macrophages. LPS treatment (10 mg/ml, 24 hours) induced an approximately 2.5-fold increase in the MAP kinase activity (FIG. 8), without affecting the amount of immunoreactive MAP kinase content, as demonstrated by Western blotting (not shown). Pretreatment of the cells for 3 days with INH$_2$BP (150 mM) suppressed basal MAP kinase activity by approximately 50% and abolished the LPS-induced increase in MAP kinase (not shown). Basal MAP kinase activity was slightly suppressed by the MAP kinase kinase inhibitor; Pang et al., 1995, "Inhibition of MAP kinase kinase blocks the differentiation of PC-12 cells induced by nerve growth factor," *J. Biol. Chem.* 270:13585–8; PD 98059 (100 mM), and LPS-induced MAP kinase activation was also inhibited (FIG. 8). In agreement with recent data in cardiac myocytes; Singh et al., 1996, "Regulation of cytoline-inducible nitric oxide synthesis in cardiac myocytes and microvascular endothelial cells.," *J. Biol. Chem.* 271:1111–1117; LPS-induced nitrite production was also suppressed by PD 98059 (by 53%, at 100 mM, n=3).

Figure 9:
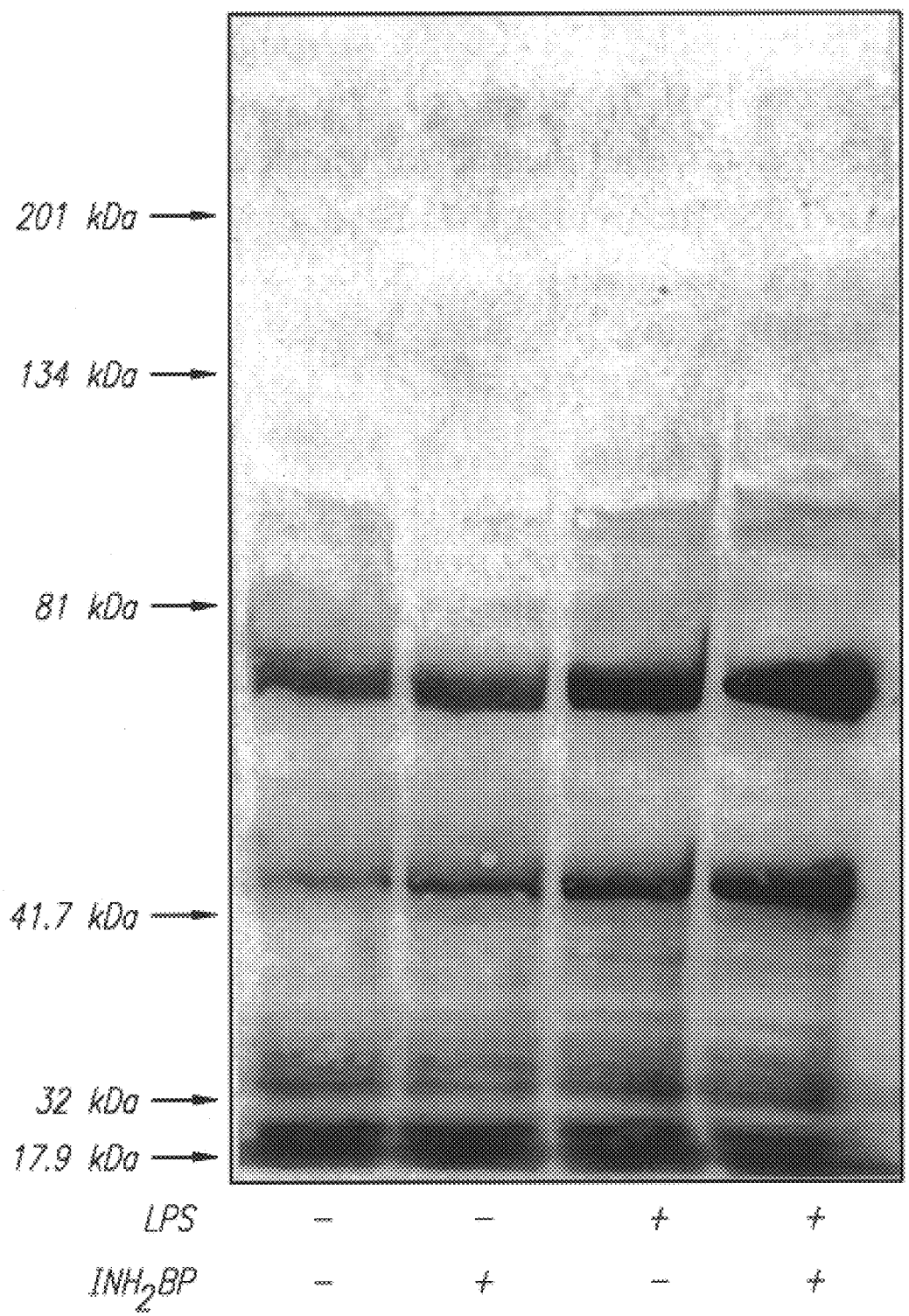
FIG. 9. Inhibition of pADPRT with $INH_2BP$ does not alter the nuclear translocation of NF-κB Western blot of nuclear extracts of control J74 cells and in cells at 90 min. after LPS treatment in the presence or absence of $INH_2BP$ (100 μM).

Similar to recent observations in a range of monocytic cell lines; Baeuerle et al., 1994, "Function and activation of NF-B in the immune system," *Ann. Rev. Immunol.* 12:141–79; we found basal (constitutive) nuclear NF-kB in the J774 cells and RAW 264.7 cells. LPS stimulation caused an increase in nuclear translocation of NF-kB, and inhibition of INH$_2$BP did not affect nuclear translocation of NF-kB in response to LPS (FIG. 9).

DISCUSSION

Poly(ADP-ribose) synthetase (pADPRT) is a protein-modifying and ADP-polymerizing enzyme which is present abundantly in the nucleus; Ueda et al., 1985, "ADP-ribosylation," *Ann. Rev. Biochem.* 54:73–100. The physiological function of pADPRT has been the subject of much debate. In contrast to the original proposal, which claimed that pADPRT is a DNA repair enzyme, now it is clear that pADPRT is not directly involved in DNA repair; Lindahl et al., 1995, "Post-translational modification of poly(ADP-ribose) polymerase induced by DNA strand breaks," *Trends Biochem. Sci.* 20:405–411; and cells from transgenic mice in which the pADPRT gene has been ablated have normal DNA repair characteristics; Buki et al., 1995, "Identification of domains of poly(ADP-ribose) polymerase for protein binding and self association." *J. Biol. Chem.* 270:3370–3377. Under physiologic conditions pADPRT can bind to numerous cellular protein and DNA site and can exert pleitropic cellular regulatory functions; Bauer et al., 1995, "Modification of growth related enzymatic pathways and apparent loss of tumorigenicity of a ras-transformed bovine endothelial cell line by treatment with 5-iodo-6-amino-1,2-benzopyrone (INH$_2$BP)," *Int. J. Oncol.* 8:239–252; Bauer et al., 1995, "Reversal of malignant phenotype by 5-iodo-6-amino-1,2-benzopyrone, a non-covalently binding ligand of poly (ADP-ribose) polymerase," *Biochimie* 77:347–377; Buki et al., 1995, "Identification of domains of poly(ADP-ribose) polymerase for protein binding and self association," *J. Biol. Chem.* 270:3370–3377. pADPRT activation has also been proposed to serve as a mechanism to induce cell death, in particular after radiation injury, and oxidant stress; Cochrane, 1991, "Mechanisms of oxidant injury of cells." *Molec. Aspects Med.* 12:137–147; Berger, 1991, "Oxidant-induced cytotoxicity: a challenge for metabolic modulation," *Am. J. Respir. Cell. Mol. Biol.* 4:1–3. One of the important physiological functions of pADPRT may be the regulation of enzyme induction, gene expression and cell differentiation; Bauer et al., 1995, "Modification of growth related enzymatic pathways and apparent loss of tumorigenicity of a ras-transformed bovine endothelial cell line by treatment with 5-iodo-6-amino-1,2-benzopyrone (INH$_2$BP)," *Int. J. Oncol.* 8:239–252.; Bauer et al., 1995, "Reversal of malignant phenotype by 5-iodo-6-amino-1,2-benzopyrone, a non-covalently binding ligand of poly (ADP-ribose) polymerase," *Biochimie* 77:347–377; Minaga et al., 1978, "Induction of cardiac L-ornithine decarboxylase by nicotinamide and its regulation by putrescine," *Eur. J. Biochem.* 91:577–85; Griffin et al., 1984, "The in vivo effect of benzamide and phenobarbital on liver enzymes: poly (ADP-ribose) polymerase, cytochrome P-450, styrene oxide hydrolase, cholesterol oxide hydrolase, cholesterol oxide hydrolase, glutathione S-transferase and UDP-glucuronyl transferase," *Biochem. Biophys. Res. Comm.* 122:770–5. The induction of alkaline phosphatase by INH$_2$BP; Bauer et al., 1995, "Modification of growth related enzymatic pathways and apparent loss of tumorigenicity of a ras-transformed bovine endothelial cell line by treatment with 5-iodo-6-amino-1,2-benzopyrone (INH$_2$BP)," *Int. J. Oncol.* 8:239–252; is a probable cause of inactivation of certain phosphorylation dependent enzymes, e.g., MAP kinase topoisomerase I and topoisomerase II. INH$_2$BP in bovine endothelial cells transfected with Ha-ras abrogates tumorigenicity, arrests cell multiplication, increases toposomerase I, toposomerase II, and MAP kinase activity, down-regulates DNA-methyl-transferase and protein kinase C, and ODC increases the hypophosphorylation of Rb protein, and inhibits the expression of the ras gene without the loss of the oncogene, Bauer et al., 1995, "Modification of growth related enzymatic pathways and apparent loss of tumorigenicity of a ras-transformed bovine endothelial cell line by treatment with 5-iodo-6-amino-1,2-benzopyrone (INH$_2$BP)," *Int. J. Oncol.* 8:239–252; Bauer et al., 1995, "Reversal of malignant phenotype by 5-iodo-6-amino-1,2-benzopyrone, a non-covalently binding ligand of poly (ADP-ribose) polymerase," *Biochimie* 77:347–377.

Based on the recently described anticancer actions of INH$_2$BP; Bauer et al., 1995, "Modification of growth related enzymatic pathways and apparent loss of tumorigenicity of a ras-transformed bovine endothelial cell line by treatment with 5-iodo-6-amino-1,2-benzopyrone (INH$_2$BP)," *Int. J. Oncol.* 8:239–252; Bauer et al., 1995, "Reversal of malignant phenotype by 5-iodo-6-amino-1,2-benzopyrone, a non-covalently binding ligand of poly (ADP-ribose) polymerase," *Biochimie* 77:347–377; and the link between chronic inflammation and cancer, with special reference to NO production (see: Introduction), here we investigated whether INH$_2$BP modulates the LPS-induced inflammatory response in vitro and in vivo. We found that several of the pathways and mediators studied (MAP kinase, prostaglandins, NO) were suppressed by INH$_2$BP, whereas others (TNF, IL-6, NF kB) were unaffected, or augmented (IL-10). Generally, the present data of the invention shows that pADPRT inhibitory compounds such as INH$_2$BP exert anti-inflammatory actions, and the combination of these effects may underlie the improvement in survival rate in the animals or mammals pretreated with this inhibitor of pADPRT.

EXAMPLE 2

INH$_2$BP Suppresses the LPS-induced Induction of iNOS

By way of background, the inducible isoform of nitric oxide (NO) synthease (iNOS) is expressed in response to pro-inflammatory stimuli in a variety of cells. Overproduction of NO by iNOS plays an important role in shock and inflammation; Nathan, 1992, "Nitric oxide as a secretory product of mammalian cells," *FASEB J.* 6:3051–3064; Vane, J. R., The Croonian Lecture 1993, "The endothelium: maestro of the blood circulation," *Proc. Roy. Soc. Lond B* 343:225–246; Szabo, C.; 1995, "Alterations in the production of nitric oxide in various forms of circulatory shock," *New Horizons* 3:3–32; and may predispose to carcinogenic transformation; Bartsch et al., 1994, "Endogenously formed N-nitroso compounds and nitrosating agents in human cancer etiology," *Pharmacogenetics* 2:272–7; Liu et al., 1992, "Woodchuck hepatitis virus surface antigen induces NO synthesis in hepatocytes: possible role in hepatocarcinogenesis.," *Carcinogenesis* 15:2875–7; Ohshima et al., 1994, "Chronic infections and inflammatory processes as cancer risk factors: possible role of nitric oxide in carcinogenesis," *Mutation Res.* 305:253–64. The promoter region of the murine iNOS gene has been cloned, and separate regions responsible for inducibility in response to LPS and to IFN have been identified. LPS-mediated induction if iNOS appears to involve the mobilization and nuclear translocation of NF-kB, with subsequent binding to the iNOS promoter. The induction of iNOS can also be inhibited by pharmacological inhibitors of tyrosine kinase and NF-kB activation; Szabo, C.; 1995, "Alterations in the production of nitric oxide in various forms of circulatory shock," *New Horizons* 3:3–32.

The inhibitory effect of INH$_2$BP on iNOS expression was indicated by the inhibition on nitrite production., iNOS mRNA expression and iNOS protein expression. The regulation occurs in the early stage of iNOS induction, since INH$_2$BP gradually loses its effectiveness when applied at increasing times after the stimulus for iNOS induction. The regulation of INH$_2$BP of iNOS induction occurs both in vitro and in whole animals. In addition, our data show that the LPS-induced production of cyclooxygenase metabolites, similar to the induction of iNOS, is modulated by INH$_2$BP. The production of cyclooxygenase metabolites by pro-inflammatory cytokines is due to novel mRNA and protein synthesis, and expression of COX-2, by a process which shares similarities with the process of iNOS induction; Vane et al., 1995, "New insights into the mode of action of anti-inflammatory drugs," *Inflamm. Res.* 44:1–10. The inhibition of the LPS-induced expression of inflammatory mediators, however, is not a non-specific response to INH$_2$BP, since the induction of TNF by LPS was not affected by this agent in the J774 cells.

Interestingly, the inhibitory effect of INH$_2$BP on iNOS was greatly reduced when LPS was used in combination with INF for immunostimulation. This effect may be due to the fact that IFN-induced transcription factors such as interferon-regulatory factor; Martin et al., 1994, "Role of interferon regulatory factor 1 in induction of nitric oxide synthase," *J. Exp. Med.* 180:977–84; bypass the inhibition of the iNOS induction by the above mentioned agents.

Previous in vitro studies have suggested that induction of iNOS is modulated by pharmacological inhibitors of pADPRT in macrophages in vitro; Hauschildt et al., 1992, "Induction of nitric oxide synthase in L929 cells by tumour-necrosis factor alpha is prevented by inhibitors of poly (ADP-ribose) polymerase," *Biochem. J.* 288:255–260; Pellat-Seceunyk et al., 1994, "Nicotinamide inhibits nitric oxide synthase mRNA induction in activated macrophages," *Biochem. J.* 297:53–58. However, in these studies, the pADPRT inhibitors 30 aminobenzamide and nicotinamide were used at high concentrations (10–30 mM), which inhibited total protein and RNA synthesis, and may have had additional, pharmacological actions, such as free radical scavenging; Hauschildt et al., 1992, "Induction of nitric oxide synthase in L929 cells by tumour-necrosis factor alpha is prevented by inhibitors of poly (ADP-ribose) polymerase," *Biochem. J.* 288:255–260. The present experiments, using INH$_2$BP, further suggest the pleiotropic involvement of pADPRT in the process of iNOS mRNA transcription. In order to study the regulation of the iNOS promoter by INH$_2$BP, transient transfection assays were performed using murine macrophage iNOS promoter luciferase constructs. These data with the deletional constructs indirectly suggest that INH$_2$BP regulates a transcription event which involves the murine iNOS promoter region between –1592 and –367 bp. ADP-ribosylation of histones and nucleases may be involved in the maintenance of a relaxed chromatin structure; Bauer et al., 1995, "Modification of growth related enzymatic pathways and apparent loss of tumorigenicity of a ras-transformed bovine endothelial cell line by treatment with 5-iodo-6-amino-1,2-benzopyrone (INH$_2$BP)," *Int. J. Oncol.* 8:239–252; Bauer et al., 1995, "Reversal of malignant phenotype by 5-iodo-6-amino-1,2-benzopyrone, a non-covalently binding ligand of poly (ADP-ribose) polymerase," *Biochimie* 77:347–377; Ueda et al., 1985, "ADP-ribosylation," *Ann. Rev. Biochem.* 54:73–100. Based on previous experimental data; Bauer et al., 1995, "Modification of growth related enzymatic pathways and apparent loss of tumorigenicity of a ras-transformed bovine endothelial cell line by treatment with 5-iodo-6-amino-1,2-benzopyrone (INH$_2$BP)," *Int. J. Oncol.* 8:239–252; Bauer et al., 1995, "Reversal of malignant phenotype by 5-iodo-6-amino-1,2-benzopyrone, a non-covalently binding ligand of poly (ADP-ribose) polymerase," *Biochimie* 77:347–377; is reasonable to suggest that in these experimental systems pADPRT inhibitory compounds, e.g., INH$_2$BP, pretreatment inhibits auto-poly-ADP-ribosylation of pADPRT and histones. Such action is known to trigger the conversion of relaxed to condensed chromatin, and, by way of upregulation of nucleases and other DNA structure regulatory enzymes; Bauer et al., 1995, "Modification of growth related enzymatic pathways and apparent loss of tumorigenicity of a ras-transformed bovine endothelial cell line by treatment with 5-iodo-6-amino-1,2-benzopyrone (INH$_2$BP)," *Int. J. Oncol.* 8:239–252; Bauer et al., 1995, "Reversal of malignant phenotype by 5-iodo-6-amino-1,2-benzopyrone, a non-covalently binding ligand of poly (ADP-ribose) polymerase," *Biochimie* 77:347–377; may affect promoter functions.

EXAMPLE 3

Effect of Inhibition of $INH_2BP$ on MAP Kinase and NF-kB Activation

These results have demonstrated that $INH_2BP$ treatment inhibits LPS-induced activation of MAP kinase. In respect, these data are similar to findings with transformed endothelial cells; Bauer et al., 1995, "Modification of growth related enzymatic pathways and apparent loss of tumorigenicity of a ras-transformed bovine endothelial cell line by treatment with 5-iodo-6-amino-1,2-benzopyrone ($INH_2BP$)," *Int. J. Oncol.* 8:239–252. It is probable that the inhibition of MAP kinase activation occurs by a pleiotropic cellular response trigger by $INH_2BP$. MAP kinase has been shown to be activated in various cell types treated with LPS or various pro-inflammatory cytokines (TNF-alpha, interleukin-1, nerve growth factor); Kyriakis et al., 1996, "Sounding the alarm: protein kinase cascades activated by stress and inflammation," *J. Biol Chem.* 271:24313–24316; Matsuda et al., 1994, "Signaling pathways mediated by the mitogen-activated protein (MAP) kinase kinase/MAP kinase cascade," *J. Leukocyte Biol.* 56:548–53; Cowley et al., 1994, "Activation of MAP kinase kinase is necessary and sufficient for PC12 differentiation and for transformation of NIH 3T3 cells.," *Cells* 77:841–52; Pang et al., 1995, "Inhibition of MAP kinase kinase blocks the differentiation of PC-12 cells induced by nerve growth factor," *J. Biol. Chem.* 270:13585–8; Willis et al., 1996, "Differential induction of the mitigen-activated protein kinase pathway by bacterial lipopolysaccharide in cultured monocytes and astrocytes," *Biochem. J.* 313:519–524; Saklatvala et al., 1993, "Interleukin 1 and tumour necrosis factor-alpha activate the mitogen-activated protein (MAP) kinase kinase in cultured cells," *FEBS Lett.* 334:189–92. A variety of extracellular signals converge at the MAP kinase kinase/MAP kinase cascade through different MAP kinase kinase-kinases and elicit a wide spectrum of cellular responses; Kyriakis et al., 1996, "Sounding the alarm: protein kinase cascades activated by stress and inflammation," *J. Biol Chem.* 271:24313–24316; Ferrell, J E, 1996, "Tripping the switch fantastic: how a protein kinase cascade can convert graded inputs into switch-like outputs," *TIBS* 21:460–466. Blockade of MAP kinase or MAP kinase kinase modifies a multitude of intracellular pathways and inhibits cellular differentiation and proliferation; Kyriakis et al., 1996, "Sounding the alarm: protein kinase cascades activated by stress and inflammation," *J. Biol Chem.* 271:24313–24316; Matsuda et al., 1994, "Signaling pathways mediated by the mitogen-activated protein (MAP) kinase kinase/MAP kinase cascade," *J. Leukocyte Biol.* 56:548–53; Cowley et al., 1994, "Activation of MAP kinase kinase is necessary and sufficient for PC12 differentiation and for transformation of NIH 3T3 cells.," *Cells* 77:841–52; Pang et al., 1995, "Inhibition of MAP kinase kinase blocks the differentiation of PC-12 cells induced by nerve growth factor," *J. Biol. Chem.* 270:13585–8; Willis et al., 1996, "Differential induction of the mitigen-activated protein kinase pathway by bacterial lipopolysaccharide in cultured monocytes and astrocytes," *Biochem. J.* 313:519–524; Saklatvala et al., 1993, "Interleukin 1 and tumour necrosis factor-alpha activate the mitogen-activated protein (MAP) kinase kinase in cultured cells," *FEBS Lett.* 334:189–92. Recently, inhibition of MAP kinase with PD 98059 has been shown to suppress the expression of iNOS mRNA in cultured endothelial cells and a cardiac myocytes; Singh et al., 1996, "Regulation of cytoline-inducible nitric oxide synthesis in cardiac myocytes and microvascular endothelial cells.," *J. Biol. Chem.* 271:1111–1117. This finding is in line with our observation that PD 98059 causes a marked suppression of nitrite production by LPS in the RAW macrophages.

Since activation of NF-kB is a major pathway in the inflammatory response, and it is involved in the induction of iNOS by LPS, but not by INF; Szabo, C.; 1995, "Alterations in the production of nitric oxide in various forms of circulatory shock," *New Horizons* 3:3–32; Martin et al., 1994, "Role of interferon regulatory factor 1 in induction of nitric oxide synthase," *J. Exp. Med.* 180:977–84, we sought to investigate potential effect of $INH_2BP$ on NF-kB. Our results demonstrate that $INH_2BP$ does not alter the nuclear translocation of NF-kB activation, or the modulation of NF-kB-mediated cellular events by $INH_2BP$, if any, may occur at a cellular event distal to nuclear translocation of NF-kB.

EXAMPLE 4

Pathophysiological and Therapeutic Implications; $INH_2BP$ Modulates the Inflammatory Process at Multiple Levels Reduction by pADPRT inhibitors of the expression of pro-inflammatory genes iNOS and COX-2, and the subsequent reduced formation of NO and prostaglandins may be beneficial in various forms of inflammation; Nathan, 1992, "Nitric oxide as a secretory product of mammalian cells," *FASEB J.* 6:3051–3064; Vane, J. R., The Croonian Lecture 1993, "The endothelium: maestro of the blood circulation," *Proc. Roy. Soc. Lond B* 343:225–246; Szabo, C.; 1995, "Alterations in the production of nitric oxide in various forms of circulatory shock," *New Horizons* 3:3–32; Vane et al., 1995, "New insights into the mode of action of anti-inflammatory drugs," *Inflamm. Res.* 44:1–10. In addition, enhanced release of IL-10 may have additional anti-inflammatory actions; Liles et al., 1995, "Review: nomenclature and biologic significance of cytokines involved in inflammation and the host immune response," *J. Infect Dis.* 172:1573–80; Giroir, 1993, "Mediators of septic shock: new approaches for interrupting the endogenous inflammatory cascade," *Critical Car. Med.* 21:780–9; Szabo et al., 1997, "Isoproterenal regulates tumour necrosis factor, interleukin-10, interleukin-6 and nitric oxide production and protects against the development of vascular hyporeactivity in endotoxemia," *Immunology* 90:95–100. It is conceivable that such effects significantly contribute to the improvement by pADPRT inhibitory compounds, e.g., $INH_2BP$ pretreatment and the survival rate of mice challenged with lethal doses of endotoxin. However, the delineation of the exact mechanisms by which $INH_2BP$ exerts effects on the LPS-induced expression of the various inflammatory mediators requires further detailed investigations. On one hand, it is conceivable that pADPRT activity or the binding of pADPRT protein is involved in the regulation of the production of inflammatory mediators and/or the expression of genes that code for components of the inflammatory process. On the other hand, it is probable that indirect down-regulation of MAP kinase activity by $INH_2BP$; Bauer et al., 1995, "Modification of growth related enzymatic pathways and apparent loss of tumorigenicity of a ras-transformed bovine endothelial cell line by treatment with 5-iodo-6-amino-1,2-benzopyrone ($INH_2BP$)," *Int. J. Oncol.* 8:239–252; may also contribute to the observed effects, as predicted by other studies; Kyriakis et al., 1996, "Sounding the alarm: protein kinase cascades activated by stress and inflammation," *J. Biol Chem.* 271:24313–24316; Ferrell, J E, 1996, "Tripping the switch fantastic: how a protein kinase cascade can convert graded inputs into switch-like outputs," *TIBS* 21:460–466. The present results demonstrate the therapeutic potential of pADPRT inhibitory compounds such as INH$_2$BP in various inflammatory diseases.

EXAMPLE 5

Some of the cytotoxic effects of nitric oxide (NO) are related to the production of peroxynitrite, a reactive oxidant formed by the rapid reaction of NO and superoxide; Crow et al., 1995, "The role of peroxynitrite in nitric oxide-mediated toxicity", *Current Top Microbiol. Immunol.* 196:57–73; Pryor et al., 1995, "The chemistry of peroxynitrite: a product from the reaction of nitric oxide with superoxide", *Am. J. Physiol.* L699–L772. The formation of peroxynitrite has been demonstrated in a variety of inflammatory conditions, including systemic inflammation induced by endotoxin; Szabo et al., 1995, "Alterations in nitric oxide production in various forms of circulatory shock" *New Horizons* 3:2–32; arthritis; Kaur et al., "Evidence for nitric oxide-mediated oxidative damage in chronic inflammation. Nitrotyrosine in serum and synovial fluid from rheumatoid patients", *FEBS Lett.* 1359:9–12; and carageenan induced paw edema; *Salvemini et al., 1996. In fact, from pharmacological studies, utilizing NO synthase (NOS) inhibitors and superoxide dismutase mimetics, it was concluded that peroxynitrite plays an important pathogenetic role in the development of in the inflammatory process; Szabo C, 1996, "The role of peroxynitrite in the pathophysiology of shock, inflammation and schemia-reperfusion injury", *Shock* 6:79–88; *Salvemini et al., 1996; *Zingarelli et al., 1997. Moreover, it has been demonstrated that some of the agents currently used in the treatment of arthritis are, in fact, scavengers of peroxynitrite; Whiteman et al., 1996 "Protection against peroxynitrite dependent tyrosine nitration and alpha 1-antiproteinase inactivation by some anti-inflammatory drugs and by the antibiotic tetracycline" *Annals. of the Rheumatic Diseases* 55:383–7. The realization that a significant part of the NO-related cytotoxicity is due to the formation of peroxynitrite has necessitated the development of novel therapeutic approaches based around the formation and action of peroxynitrite.

One of the intracellular pathways triggered by peroxynitrite is related to DNA single strand breakage and activation of poly (ADP-ribose) synthetase (PARS); Szabo et al., 1996, "The role of peroxynitrite in the pathophysiology of shock, inflammation and schemia-reperfusion injury", *Shock* 6:79–88; *Szabo, 1996b). Pronounced activation of PARS can rapidly deplete the intracellular concentration if its substrate, NAD$^+$, slowing the rate of glycolysis, electron transport, and, therefore, ATP formation, resulting in cell dysfunction; *Berger, 1991; *Cochrane, 1991. Accordingly, inhibitors of PARS protect against cellular injury under these conditions. This mechanism, known as the "PARS suicide hypothesis", has previously been characterized in relation to H$_2$O$_2$-induced oxidant damage and radiation injury; *Berger, 1991; *Cochrane, 1991; and has recently been implicated in the NO- and peroxynitrite-related cellular injury in endotoxic shock, stroke, ischemia-reperfusion injury, and diabetes mellitus; Szabo et al., 1996, "The role of peroxynitrite in the pathophysiology of shock, inflammation and schemia-reperfusion injury", *Shock* 6:79–88; *Zhang et al., 1994, *Heller, et al., 1995.

The potential role of PARS in arthritis has recently been put forward by Kroger and colleagues. In a potassium peroxochromate-induced model, nicotinamide treatment caused 1 25–35% reduction in the mean arthritic score; *Miesel et al., 1996. However, from that study, the mechanism of the inhibition remained undefined, since no clear distinction could be drawn between the free radical scavenging activity and the PARS inhibitory effect of nicotinamide; *Miesel et al., 1995. In the present study, with the aid of 5-iodo-6-amino-1,2-benzopyrone (INH$_2$BP), a novel, potent inhibitor of PARS activity; *Bauer et al., 1995a, *Bauer et al., 1995b; we investigated the effect of pharmacological inhibition of PARS on the course of carrageenan-induced paw edema and collagen-induced arthritis. The results of our study support the view that inhibition of PARS is of antiinflammatory potential.

EXAMPLE 6

Induction and Evaluation of Carrageenan-induced Paw Edema

Male Wistar rats (250–300 g, Charles River Laboratories, Wilmington, Mass.) were used in these studies. Animals received a subplantar injection 0.1 ml saline containing 1% 1-carrageenan into the right hind paw. This phlogogenic agent was given to either INH$_2$BP-treated animals or to animals treated with vehicle. Animals were treated with INH$_2$BP (o.5 g/kg p.o) −24 h and −2 h before the injection of carrageenan. The volume of the paw was measured by phlethysmometry immediately after the injection as previously described; *Sautebin, et al., 1995. Subsequent readings of the volume of the same paw were carried out at 60 minute intervals and compared to the initial readings. For these experiments, n=6 vehicle-treated and n=6 INH$_2$BP treated animals were used.

EXAMPLE 7

Induction and Evaluation of Collagen-induced Arthritis

Male DBA/1J mice (9 weeks, Jackson Laboratory, Bar Harbor, Me.) were used for these studies. Chick type II collagen (CII) was dissolved in 0.01 M acetic acid at a concentration of 2 mg/ml by stirring overnight at 4° C. Dissolved CII was frozen at −70° C. until use. Complete Freund's adjuvant (CFA) was prepared by the addition of *Mycobacterium tuberculosis* H37ra at a concentration of 2 mg/ml. Before injection, CII was emulsified with an equal volume of CFA. Collagen-induced arthritis was induced as previously described; Hughes et al., 1994, "Induction of T helper cell hyporesponsiveness in an experimental model of autoimmunity by using nonmitogenic anti-CD3 monoclonal antibody", *J. Immunol.* 153:3319–3325. On day 1, mice were injected intradermally at the base of the tail with 100 ml CII). On day 21, a second injection of CII in CFA was administered. Animals were treated with either vehicle (n=10) or with INH$_2$BP (n=60(0.5 g/kg p.o.) every 24 hours, starting from Day 25. Mice were evaluated daily for arthritis by using a macroscopic scoring system ranging from 0 to 4 (1—swelling and/or redness of the paw or one digit; 2—two joints involved; 3—more than two joints involved; 3—more than two joints involved; and 4=severe arthritis of the entire paw and digits). The arthritic index for each mouse was calculated by adding the four scores of the individual paws. At the end of the experiments (Day 35), animals were sacrificed under anesthesia and paws and knees were removed and fixed for histological examination. Histological examination was done by an investigator blinding for the treatment regime.

Data Analysis and Presentation

For the studies with carrageenan-induced paw edema, paw volumes in the treated and untreated groups of animals were compared with unpaired Student's test. For the arthritis studies, Mann-Whitney U-test (2-tailed, independent) was used to test the statistical differences in the arthritic indices. This nonparametric statistic was used to compare medians, rather than means, because the scale of measurement was ordinal, and the distribution values were typically nonnormally distributed; ; Hughes et al., 1994, "Induction of helper cell hyporesponsiveness in an experimental model of autoimmunity by using nonmitogenic anti-CD3 monoclonal antibody", *J. Immunol.* 153:3319–3325.

Figure 10:
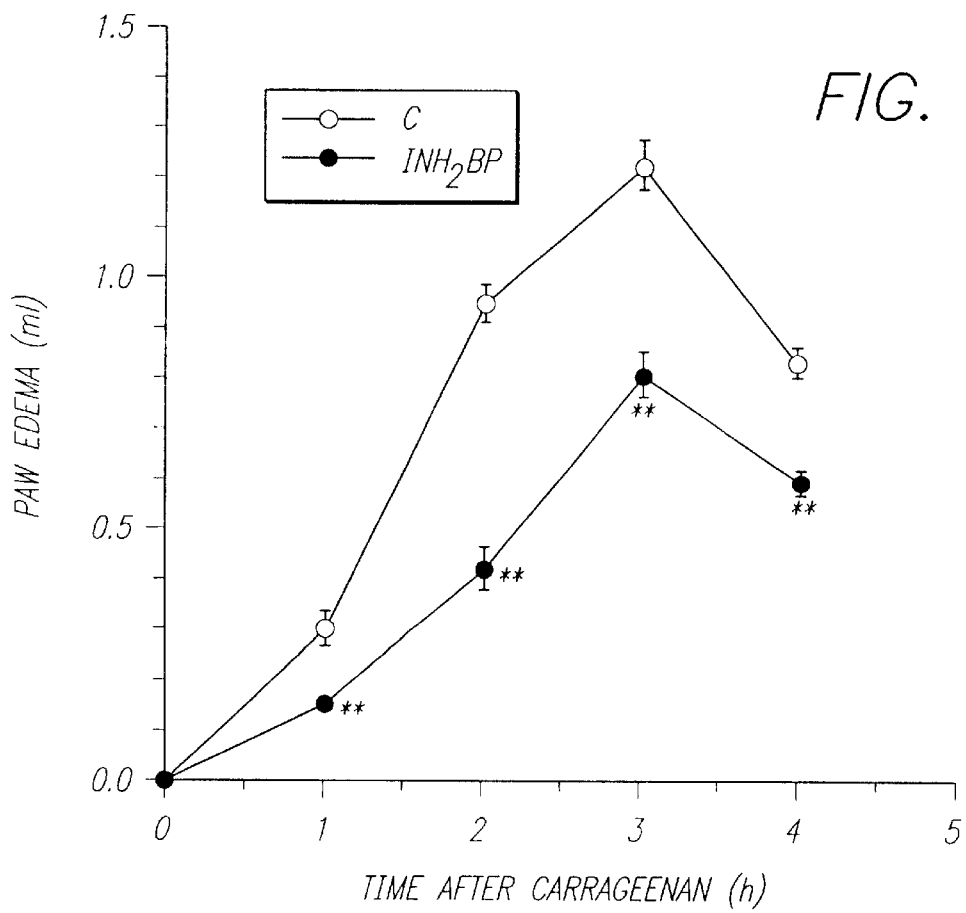
FIG. 10. Describes the effect of $INH_2BP$ on the development of carrageenan-induced paw edema. Data show paw volumes at 1–4 h after carrageenan injection (means±S.E.M., n=6 animals in each group). There was a significant increase in the paw volume from hour 1 (p<0.01), and there was a significant inhibition of the development of paw edema of $INH_2BP$ at 1–4 hours (**p<0.02).
Figure 11:
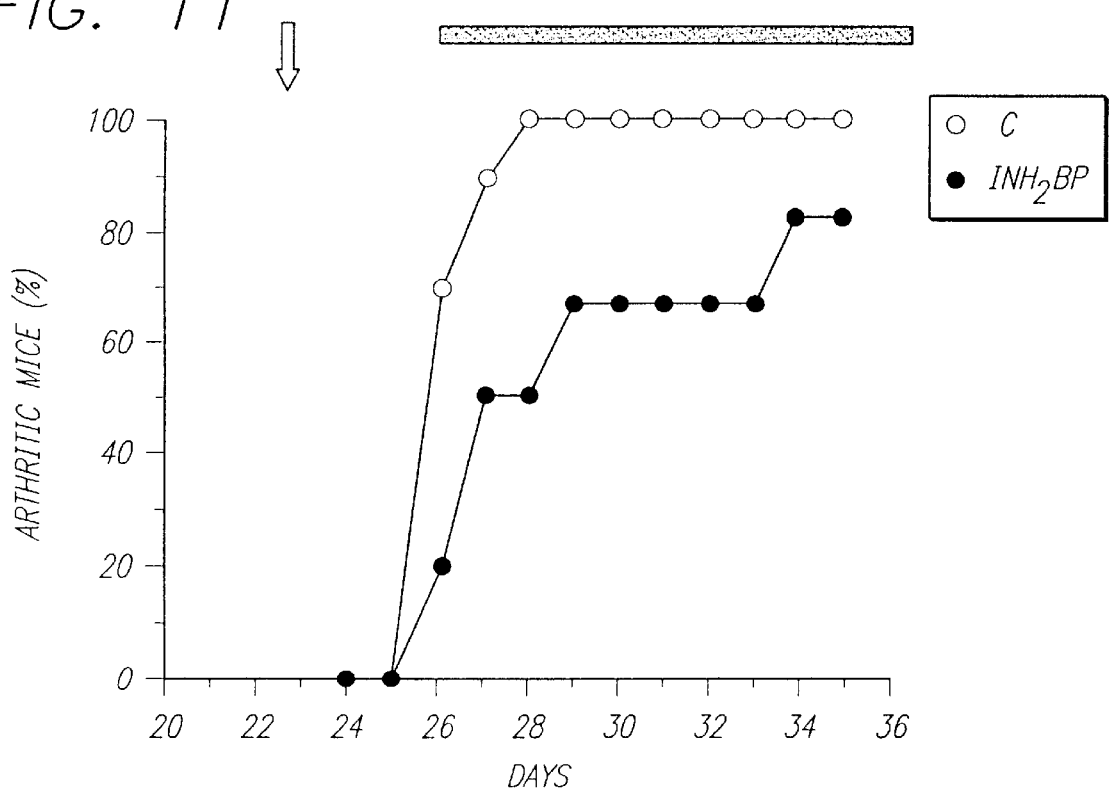
FIG. 11. Describes the effect of $INH_2BP$ on the onset of collagen-induced arthritis. The percentage of arthritic mice (mice showing clinical scores of arthritis>1) are represented. The arrow at 21 days represents the time of the second collagen immunization, the horizontal bar from day 25 represent the time of the start of treatment with $INH_2BP$ (N=6) or VEHICLE (N-10).
Figure 12:
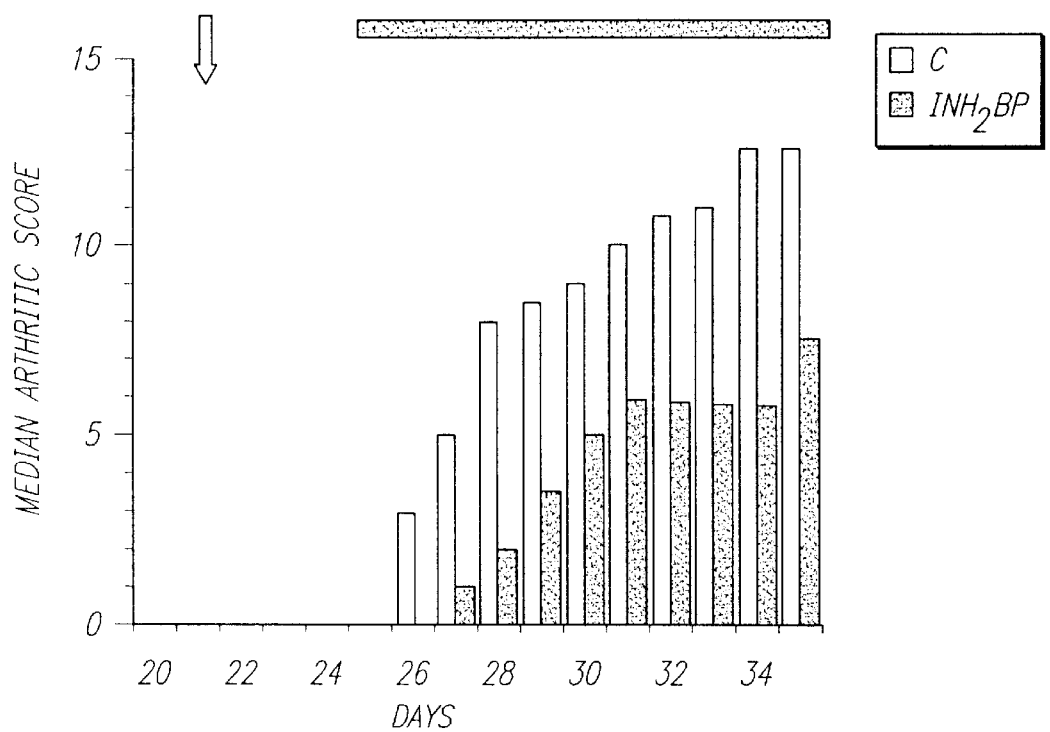
FIG. 12. Describes the effect of $INH_2BP$ on the severity of collagen-induced arthritis. Median arthritic score during collagen-induced arthritis. The arrow at 21 days represents the time of the second collagen immunization, the horizontal bar from day 25 represent the time of the start of treatment with $INH_2BP$(n-6) or vehicle (n=10). There was a significant increase in the arthritic score from day 26 (Ip<0.01), and there was a significant suppression of the arthritic score by $INH_2BP$ between days 26–35 (#p<0.05).

Values in FIG. 10 are expressed as mean±standard error of the man of n observations, where n represents the number of rats (6 animals for each group). Values in FIG. 11 represent incidences (%), whereas values in FIG. 12 represent medians. A p-value less than 0.05 was considered statistically significant (I'<0.05; **p<0.02).

Materials 5-iodo-6-amino-1,2-benzopyrone ($INH_2BP$) was prepared as described previously (*Bauer et al., 1995a; * Bauer et al., 1995b). Chick type II collagen was from Elastin Products Company, Inc. (Owensville, Mo.). *Mycobacterium tuberculosis* H37Ra was from Difco (Detroit, Mich.). All other chemicals were from Sigma Chemical Co. (St. Louis, Mo.). Subplantar injection of carrageenan into the rat paw led to a time-dependent increase in paw volume with a maximal response at 3 h (FIG. 10). This carrageenan induced paw edema was significantly reduced by treatment with $INH_2BP$ (FIG. 10).

In the collagen-induced arthritis model in mice, between Days 26–35 after the first collagen immunization, animals progressively developed arthritis, as evidenced by an increase in the arthritis incidence and an increase in the arthritic score (FIGS. 11–12). Treatment with $INH_2BP$ reduced the incidence of arthritis until Day 33 and reduced the severity of the disease throughout the experimental period. By Day 30, arthritic score increased to 10, whereas median arthritic scores in the $INH_2BP$ treated animals remained around 5 (FIG. 12). By Day 35, all vehicle-treated animals, and most of the $INH_2BP$ treated animals had some degree of arthritis (FIG. 11). However, even at Day 35, the median arthritic scores were significantly decreased by $INH_2BP$ treatment (FIG. 12).

At Day 35, histological evaluation of the paws in the vehicle-treated arthritic animals revealed signs of severe suppurative arthritis, with massive mixed (neutrophil, macrophages and lymphocyte) infiltration into the larger ankle joints and the terminal digits. In addition, a severe or moderate necrosis, hyperplasia and sloughing of the synovium could be seen, together with the extension of the inflammation into the adjacent musculature with fibrosis and increased mucous production. In the $INH_2BP$ animals, the degree of arthritis was significantly reduced. Nevertheless, there was still a significant degree of arthritis in these animals, with a moderate, primarily neutrophil infiltration into several of the larger joints, coupled with mild to moderate necrosis and hyperplasia of the synovium. Similar to these findings in the paw, signs of severe suppurative arthritis were found in the knee, which was reduced by treatment with $INH_2BP$ (not shown).

Discussion

No, peroxynitrite, oxyradicals and products of the inducible cyclooxygenase have independently been proposed as important factors in the pathogenesis of various forms of inflammation, including arthritis (see Introduction and also: Brahn, 1991, "Animal models of rheumatoid arthritis. Clues to etiology and treatment" *Clin. Orthop. Rel. Res.* 265:42–53; Kaur et al., 1994, "Evidence for nitric oxide-mediated oxidative damage in chronic inflammation. Nitrotyrosine in serum and synovial fluid from rheumatoid patients. *FEBS Lett.* 1359:9–12; Oyanagui Y, 1994, "Nitric oxide and superoxide radical are involved in both initiation and envelopment of adjuvant arthritis in rats" *Life Sci.* 54:PL285-9; Miesel et al., 1994, "Effects of allupurinol on in vivo suppression of arthritis in mice and ex vivo modulation of phagocytic production of oxygen radicals in whole human blood", *Inflammation* 6:597–612; Whiteman et al., 1996 "Protection against peroxynitrite dependent tyrosine nitration and alpha 1-antiproteinase inactivation by some anti-inflammatory drugs and by the antibiotic tetracycline" *Annals. of the Rheumatic Diseases* 55:383–7; Anderson et al., 1996, "Selective inhibition of cyclooxygenase (COX)-2-reverses inflammation and expression of COX-2 and interleukin 6 in rat adjuvant arthritis", *J. Clin. Invest.* 97:2672–2679. The present study, demonstrating anti-inflammatory effects of $INH_2BP$ in the carrageenan-induced paw edema model and in the collagen induced arthritis model supports the view that PARS is involved in the progression of the inflammatory process and the pharmacological inhibition of PARS is of anti-inflammatory potential.

The primary mode of action of $INH_2BP$ is likely to be related to interruption of the futile intracellular cascade characterized by DNA injury. PARS activation, ADP ribosylation and $NAD^+$ and ATP depletion in various cell types of the inflamed joints. Inhibition of this pathway with various inhibitors of PARS, such as 3-aminobenzamide, nicotinamide and $INH_2BP$ has been shown to protect multiple cell types from injury; Berger, 1991; *Cochrane, 1991; Szabo et al., 1996, "The role of peroxynitrite in the pathophysiology of shock, inflammation and schemia-reperfusion injury", *Shock* 6:79–88; *Szabo, 1996b.

The overproduction of NO in inflammatory conditions is due to the suppression of the inducible isoform of NOS (iNOS); Nathan, 1992, "Nitric oxide as a secretory product of mammalian cells", *FASEB J.* 6:3051–3064; Szabo, 1995, "Alterations in nitric oxide production in various forms of circulatory shock", *New Horizons* 3:2–32; Southan, et al., 1996, "Spontaneous rearrangement of aminoakylguanidines into mercaptoalkylguadidines—a novel class of nitric oxide synthase inhibitors with selectivity toward the inducible isoform" *Br. J. Pharmacol.* 117:619–632. Several lines of evidence suggest a role for iNOS and NO overproduction in the pathogenesis of arthritis (see for reviews: Stenovic-Racic, et al., 1993, "Nitric oxide and arthritis", *Arthr. Rhemat.* 36:1036–1044; *Evans et al, 1995. First, the expression of iNOS and the production of large amounts of NO has been demonstrated in chondrocytes from experimental animals and humans (Haeselmann et al., 1994, "Nitric oxide and proteoglycan synthesis by human articular chondrocytes in alginate culture", *FEBS Lett.* 352:361–364; Sakurai et al., 1995, "Nitric oxide production and inducible nitric oxide synthase expression in inflammatory arthritis", *J. Clin. Invest.* 96:2357–63; Grabowski et al., 1996, "Nitric oxide production in cells derived from the human joint", *Br. J. Rheumatol.* 35:207–12; Murrell et al., 1996, "Nitric oxide: an important articular free radical", *J. Bone Joint Sur.—Am.*

78:265–74. Second, an increase in the circulating levels of nitrite/nitrate (the breakdown products of NO) has been demonstrated in patients with arthritis (Farrell et al., 1992, "Increased concentrations of nitrite in synovial fluid and serum samples suggest increased nitric oxide synthesis in rheumatic diseases" *Ann. Rhem. Dis.* 51:1219–22; Stichtenoth, et al, 1995, "Urinary nitrate excretion is increased in patients with rheumatoid arthritis and reduced by predisolone", *Ann. Rhem. Dis.* 54:820–4. Third, the development of arthritis has been shown to be reduced by non-isoform-selective inhibitors of NOS (*Ialenti al., 1993; McCartney-Francis et al., 1993, "Suppression of arthritis by an inhibitor of nitric oxide synthase", *J. Exp. Med.* 178:749–753; Weinberg et al., 1994, "The role of nitric oxide in the pathogenesis of spontaneous murine autoimmune disease, increased nitric oxide production and nitric oxide synthase expression in MRL-1 pr/1 pr mice, and reduction of spontaneous glomerulonephritis and arthritis by orally administered NG-monomethyl-L-arginine", *J. Exp. Med.* 1979:651–60; Stefanovic-Racic et al., 1994, "N-monomethyl arginine, an inhibitor of nitric oxide synthase, suppresses the development of adjuvant arthritis in rats" *Arthr. Rheumat.* 37:1062–9; and, more recently, by inhibitors with selectivity for iNOS (Connor et al., 1995, "Suppression of adjuvant-induced arthritis by selective inhibition of inducible nitric oxide synthase", *Eur. J. Pharmacol.* 273:15–24. In this respect it is noteworthy that pretreatment of multiple cell types with PARS inhibitors (including 3-aminobenzaminde, nicotinamide as well as INH$_2$BP) prior to immunostimulation has been shown to suppress the expression of mRNA for iNOS and reduce NO production (*Hauschildt et al., 1992, *Pellat-Seceunyk et al., 1994; Zingarelli et al., 1996, "Peroxynitrite-mediated DNA strand breakage activates poly-ADP ribosyl synthetase and causes cellular energy depletion in macrophages stimulated with bacterial lipopolysaccharide" *J. Immunol.* 156:350–358; *Szabo et al 1997. From these experimental data it may be concluded that PARS via a not yet characterized mechanism, also regulates the process of iNOS expression, and that this effect may represent an additional mode of beneficial action of PARS inhibition in various forms of inflammation. However, caution should be exercised when interpreting the above findings. For instance, in the in vitro studies quoted above, extremely high concentrations of the PARS inhibitors 3-amiobenzamide and nicotinamide were required (10–30 mM) in order to demonstrate suppression of iNOS induction. These high concentrations of these agents may have additional pharmacological actions, such as inhibition of total protein and RNA synthesis, and/or free radical scavenging actions; *Hauschildt et al., 1992, *Pellat-Seceunyk et al., 1994; Zingarelli et al., 1996, "Peroxynitrite-mediated DNA strand breakage activates poly-ADP ribosyl synthetase and causes cellular energy depletion in macrophages stimulated with bacterial lipopolysaccharide" *J. Immunol.* 156:350–358. INH$_2$BP, on the other hand, effectively suppressed the expression of iNOS even at lower, non-cytotoxic concentrations (100–300 mN). However, in the case of INH$_2$BP several modes of action should be considered, since this agent is an inducer of alkaline phosphatases, with secondary, pleiotropic modulation of cellular responses; *Bauer et al., 1996; *Szabo et al., 1997). Experiments in cells or animals with ablation of the PARS gene are required to definitely address the question as to whether inhibition of PARS per se suppresses the process of iNOS induction.

In a recent study of Ehrlich and colleagues, it was shown that in cultured rabbit synovial fibroblasts, the cytokine-induced expression of collagenase activity was suppressed by 3-aminobenzamide; *Ehrlich et al., 1995. It is now possible to determine the pharmacological action (which nevertheless, would be expected to suppress the course of the arthritis process), the property of the particular inhibitor used, or whether it is, indeed, related to a reduction of the catalytic activity of PARS. In this respect, it is noteworthy that, based on studies with pharmacological inhibitors, PARS has been implicated in the regulation of a variety of genes, including the major histocompatibility complex class II gene (*Hiromatsu et al., 1992; Taniguchi et al., 1993), ras c-myc (*Bauer et al., 1996, *Nagao et al. 1991), DNA methyltransferase gene (*Bauer et al, 1996) and protein kinase C (*Bauer et al., 1996).

Taken together, the present work demonstrated the amelioration of the development of local inflammatory response and the inhibition of the progression of collagen-induced arthritis by INH$_2$BP. Although, for the last decade, a role for PARS has been proposed in DNA repair, recent observations demonstrate that the ablation of the gene for PARS does not compromise DNA repair: PARS knockout animals appear normal and viable (*Wang et al., 1995). This observation strengthens the antiinflammatory potential of pharmacological inhibitors of PARS. PARS inhibition (as opposed to iNOS inhibition) is unlikely to interfere with the important antimicrobial effects of NO, since invading microorganisms do not contain PARS. On the other hand, PARS inhibition is not only expected to inhibit part of the oxidant-induced cytotoxicity, and thus may be more effective when applied in combination with other free radical scavengers or other immunosuppressive agents. The results of the present studies support he view that PARS inhibition, alone, or in combination with other antiinflammatory agents, represents a promising novel antiinflammatory approach.

In a similar manner as shown in the above examples, compounds of formulae II, and III are used to treat inflamation or inflammatory diseases, as well as treating gram negative and gram positive infections.

The foregoing written specification is considered to be sufficient to enable one skilled in the art to practice the invention. Indeed, various modifications of the above-described modes for carrying out the invention which are obvious to those skilled in the field of pharmaceutical cormulation or related fields are intended to be within the scope of the following claims.

We claim:
1. A method for treating inflammation or inflammatory diseases in an animal or mammal comprising the step of administering an effective amount of an pADPRT inhibitory compound to said animal or mammal.
2. The method of claim 1 wherein the pADPRT inhibitory compound is selected from the group consisting of:
a compound having the formula:

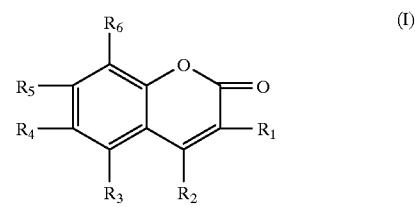

wherein $R_1$, $R_2$, $R_3$, $R_4$, $R_5$ and $R_6$ are each selected from the group consisting of hydrogen, hydroxy, amino, alkyl, alkoxy, cycloalkyl or phenol, optionally substituted with alkyl, alkoxy, hydroxy or halo, and only one of $R_1$, $R_2$, $R_3$, $R_4$, $R_5$ and $R_6$ is amino, a compound having the formula:

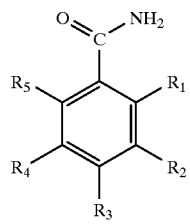

wherein $R_1$, $R_2$, $R_3$, $R_4$, and $R_5$ are each selected from the group consisting of hydrogen, hydroxy, amino, alkyl, alkoxy, cycloalkyl or phenol, optionally substituted with alkyl, alkoxy, hydroxy or halo, and only one of $R_1$, $R_2$, $R_3$, $R_4$, and $R_5$ is selected from the group consisting of amino, nitroso or nitro; and a compound having the formula:

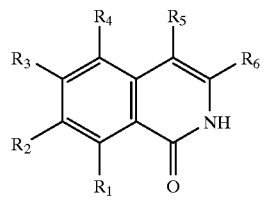

wherein $R_1$, $R_2$, $R_3$, $R_4$, and $R_5$ are each selected from the group consisting of hydrogen, hydroxy, amino, alkyl, alkoxy, cycloalkyl or phenol, optionally substituted with alkyl, alkoxy, hydroxy or halo, and only one of $R_1$, $R_2$, $R_3$, $R_4$, and $R_5$ is an amino moiety.

3. A method according to claim 2, wherein said compound is selected from the group consisting of: 6-amino-1,2-benzopyrone, 3-aminobenzamide, 5-amino-1(2H)-isoquinolinone, 7-amino-1(2H)-isoquinolinone, and 8-amino-1(2H)-isoquinolinone.

4. A method according to claim 1, wherein said compound is 5-iodo-6-amino-1,2-benzopyrone.

5. The method of claim 1 wherein the pADPRT inhibitory compound has the formula

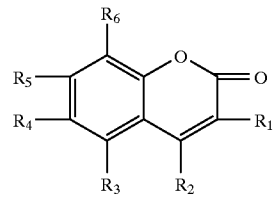

wherein $R_1$, $R_2$, $R_3$, $R_4$, $R_5$ and $R_6$ are each selected from the group consisting of hydrogen, hydroxy, amino, alkyl, alkoxy, cycloalkyl or phenol, optionally substituted with alkyl, alkoxy, hydroxy or halo, and only one of $R_1$, $R_2$, $R_3$, $R_4$, $R_5$ and $R_6$ is selected from the group consisting of amino, nitroso or nitro.

6. The method of claim 5 wherein the pADPRT inhibitory compound is 5-iodo-6-amino-1,2-benzopyrone.

7. A method of treating both gram negative and gram positive induced endotoxin symptoms in an animal or mammal, said method comprising the step of administering to a animal or mammal a therapeutically effective amount of a ADPRT inhibitory compound.

8. The method of claim 7 wherein the compound is selected from the group consisting of:

a compound having the structural formula:

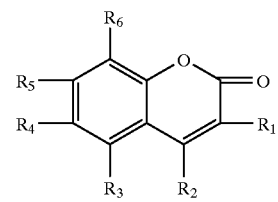

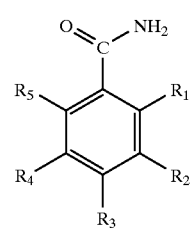

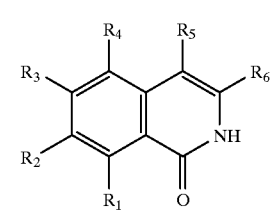

wherein $R_1$, $R_2$, $R_3$, $R_4$, $R_5$ and $R_6$ are, independent of one another, selected from the group consisting of hydrogen, hydroxy, amino, nitroso, nitro, halogen, ($C_1$–$C_6$) alkyl, ($C_1$–$C_6$) alkoxy, ($C_3$–$C_7$) cycloalkyl, and phenyl and pharmaceutically acceptable salts thereof, wherein at least three of the six $R_1$, $R_2$, $R_3$, $R_4$, $R_5$ and $R_6$ substituents are always hydrogen and at least one of the six $R_1$, $R_2$, $R_3$, $R_4$, $R_5$ and $R_6$ substituents is an amino moiety.

9. The method of claim 8, wherein the compound has the structural formula:

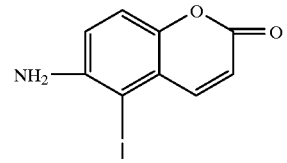

10. The method of claim 8, wherein $R_4$ is amino.

11. The method of claim 10, wherein the halogen is iodine.

* * * * *